US012600934B2

(12) United States Patent
Casura et al.

(10) Patent No.: US 12,600,934 B2
(45) Date of Patent: *Apr. 14, 2026

(54) ASEPTIC FLUID COUPLINGS

(71) Applicant: Colder Products Company, Roseville, MN (US)

(72) Inventors: Matthew Gregory Casura, St. Anthony, MN (US); Jonathan Steven Van Loon, Prescott, WI (US); Randall S. Williams, Minneapolis, MN (US)

(73) Assignee: Colder Products Company, Roseville, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/402,362

(22) Filed: Jan. 2, 2024

(65) Prior Publication Data

US 2024/0132828 A1      Apr. 25, 2024

Related U.S. Application Data

(63) Continuation of application No. 17/122,000, filed on Dec. 15, 2020, now Pat. No. 11,898,136.

(Continued)

(51) Int. Cl.
*C12M 1/12* (2006.01)
*B01L 3/00* (2006.01)
(Continued)

(52) U.S. Cl.
CPC ............. *C12M 37/02* (2013.01); *B01L 3/563* (2013.01); *C12M 23/40* (2013.01); *C12M 23/42* (2013.01);
(Continued)

(58) Field of Classification Search
CPC ....... B01L 3/563; C12M 23/40; C12M 23/42; C12M 23/46; C12M 29/04; C12M 29/26; C12M 37/04
(Continued)

(56) References Cited

U.S. PATENT DOCUMENTS 3,391,951 A    7/1968  Miller
3,466,065 A    9/1969  Acker et al.
(Continued)

FOREIGN PATENT DOCUMENTS

CN            1135710 A    11/1996
CN          101132828        2/2008
(Continued)

OTHER PUBLICATIONS

Extended European Search Report in European Appln No. 20943157. 6, dated Jan. 30, 2024, 9 pages.
(Continued)

*Primary Examiner* — Michael L Hobbs
*Assistant Examiner* — Michael A Abel
(74) *Attorney, Agent, or Firm* — Fish & Richardson P.C.

(57) ABSTRACT

Some fluid coupling devices described herein are configured for use in fluid systems. For example, some embodiments described in this document are single-use, aseptic fluid coupling devices that can be coupled to create a sterile flow path therethrough. Some such aseptic couplings are genderless couplings such that two identical aseptic couplings can be coupled together and then latched to form a robust connection between the aseptic couplings.

16 Claims, 22 Drawing Sheets

Related U.S. Application Data

(60) Provisional application No. 63/045,345, filed on Jun. 29, 2020.

(51) Int. Cl.
   *C12M 1/00*          (2006.01)
   *C12M 3/00*          (2006.01)

(52) U.S. Cl.
   CPC ............ *C12M 23/46* (2013.01); *C12M 29/04* (2013.01); *C12M 29/26* (2013.01); *C12M 37/04* (2013.01)

(58) Field of Classification Search
   USPC ...................................................... 435/297.1
   See application file for complete search history.

(56)                References Cited

U.S. PATENT DOCUMENTS

| | | | |
|---|---|---|---|
| 3,865,411 A | 2/1975 | Rowe | |
| 3,909,910 A | 10/1975 | Rowe | |
| 4,019,512 A | 4/1977 | Tenczar | |
| 4,022,205 A | 5/1977 | Tenczar | |
| 4,030,494 A | 6/1977 | Tenczar | |
| 4,565,392 A | 1/1986 | Vyse | |
| 6,655,655 B1 | 12/2003 | Matkovich et al. | |
| 7,252,308 B2 | 8/2007 | Thilly | |
| 10,369,348 B2 * | 8/2019 | Truong ................. | A61M 39/18 |
| 11,898,136 B2 * | 2/2024 | Casura ................... | B01L 3/563 |
| 2003/0030272 A1 | 2/2003 | Johnson et al. | |
| 2005/0095891 A1 | 5/2005 | Schorn | |
| 2009/0050213 A1 | 2/2009 | Biddel et al. | |
| 2009/0058103 A1 * | 3/2009 | Whitney ................. | E05C 19/14 292/247 |
| 2010/0230950 A1 * | 9/2010 | Williams .............. | A61M 39/18 285/38 |
| 2013/0289517 A1 | 10/2013 | Williams et al. | |
| 2015/0061282 A1 | 3/2015 | Faldt et al. | |
| 2016/0015911 A1 | 1/2016 | Bazargan et al. | |
| 2016/0018037 A1 | 1/2016 | Nichols | |
| 2017/0143953 A1 | 5/2017 | Williams et al. | |
| 2019/0240474 A1 * | 8/2019 | Williams ............. | A61M 39/165 |

FOREIGN PATENT DOCUMENTS

| | | |
|---|---|---|
| CN | 102405369 | 4/2012 |
| FR | 3007816 | 1/2015 |
| JP | H079128 U | 2/1995 |
| WO | WO 2010118099 | 10/2010 |

OTHER PUBLICATIONS

International Preliminary Report on Patentability in International Appln. No. PCT/US2020/065018, mailed on Jan. 12, 2023, 9 pages.
International Report on Patentability in International Application No. PCT/US2013/031418, dated Oct. 28, 2014, 5 pages.
International Search Report and Written Opinion in International Application No. PCT/US20/65018, dated Mar. 19, 2021, 10 pages.
International Search Report and Written Opinion in International Application No. PCT/US2013/031418, dated May 23, 2013, 9 pages.

* cited by examiner

130

131

133

130

133

130

131

134

135

132a

132b

130

131

135

132a

132

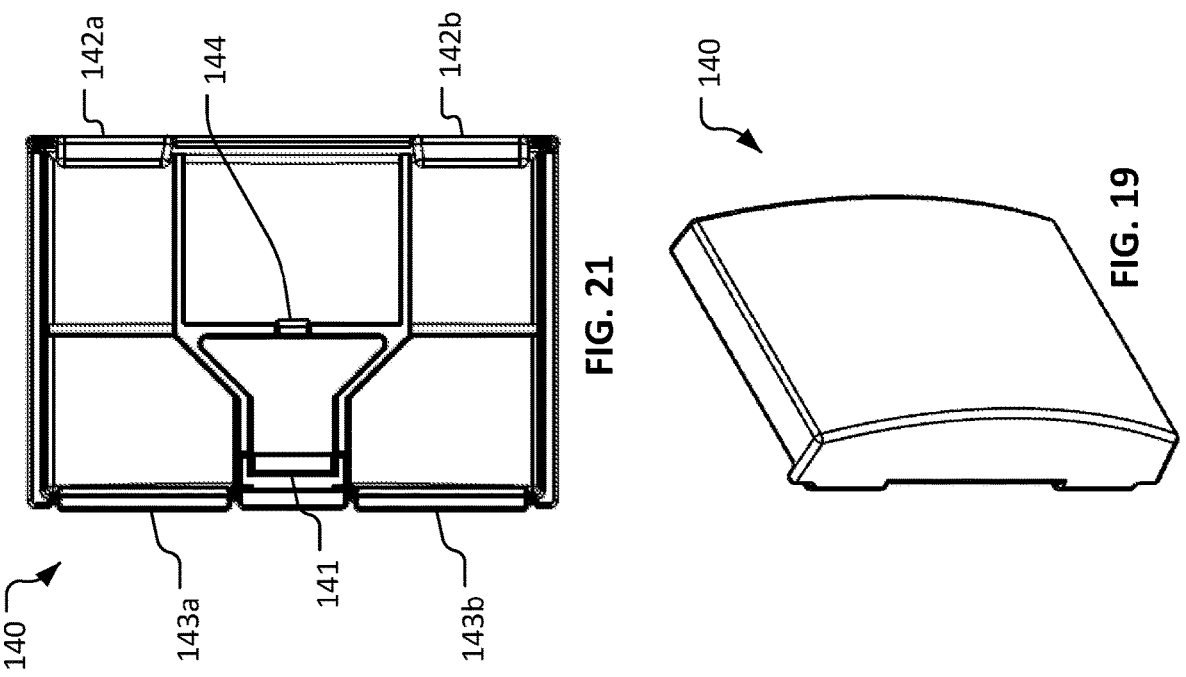
FIG. 21
FIG. 19
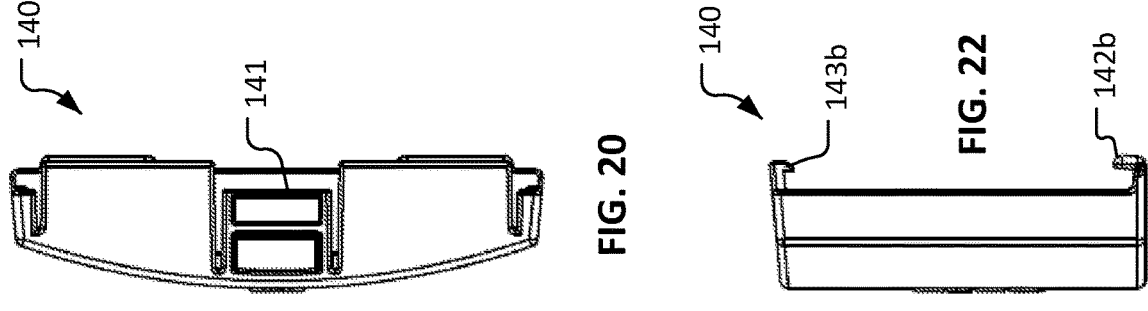
FIG. 20
FIG. 22

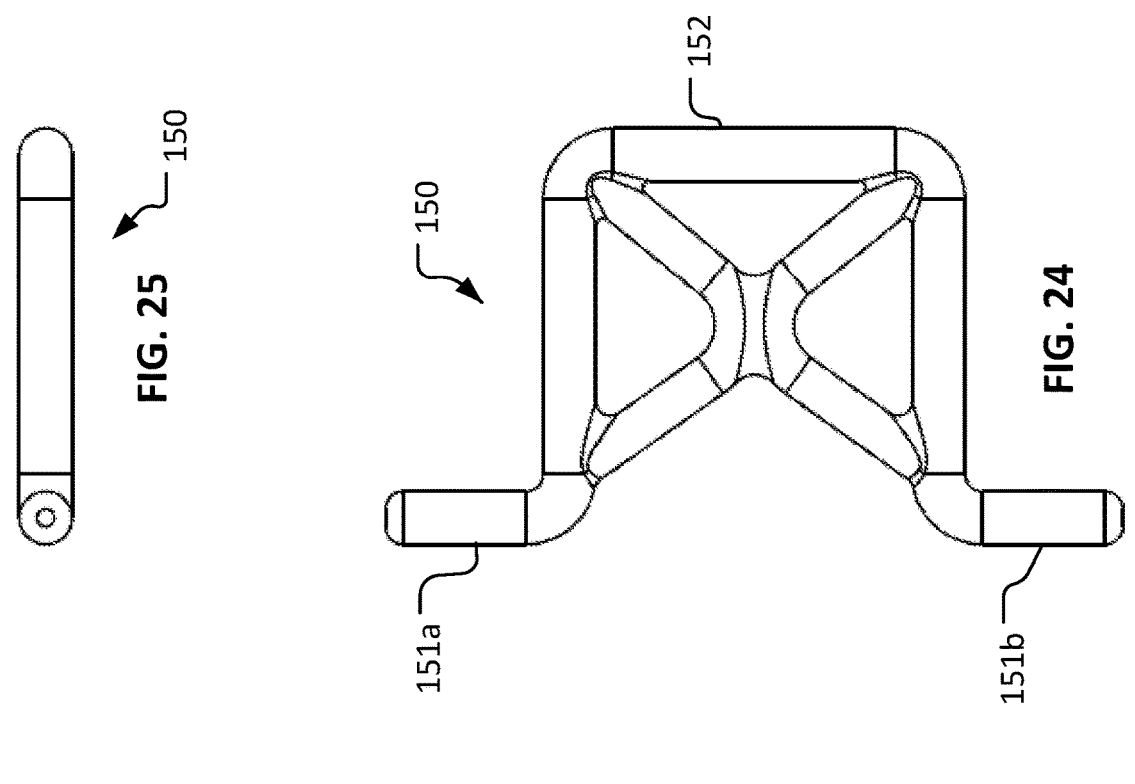
FIG. 25
FIG. 24
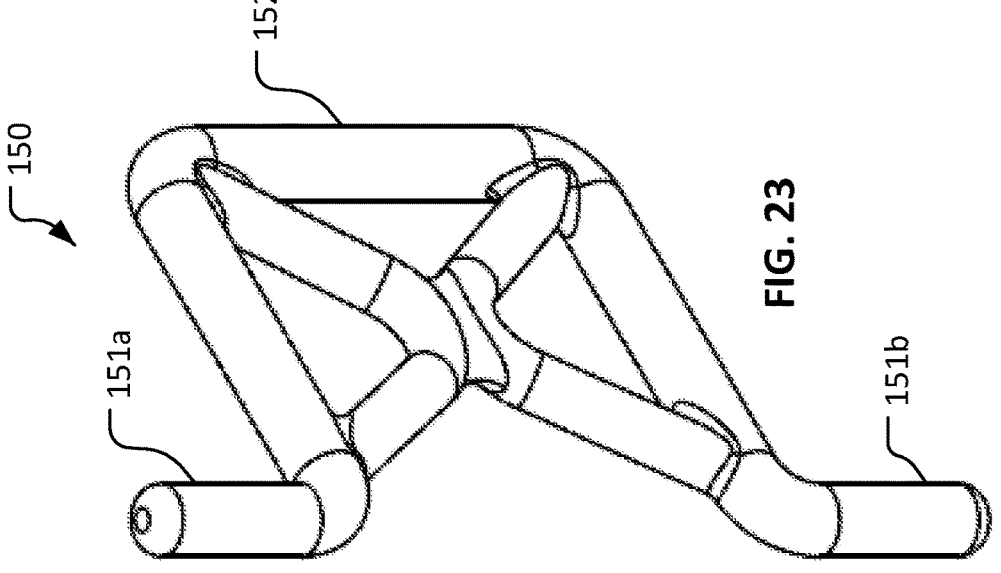
FIG. 23

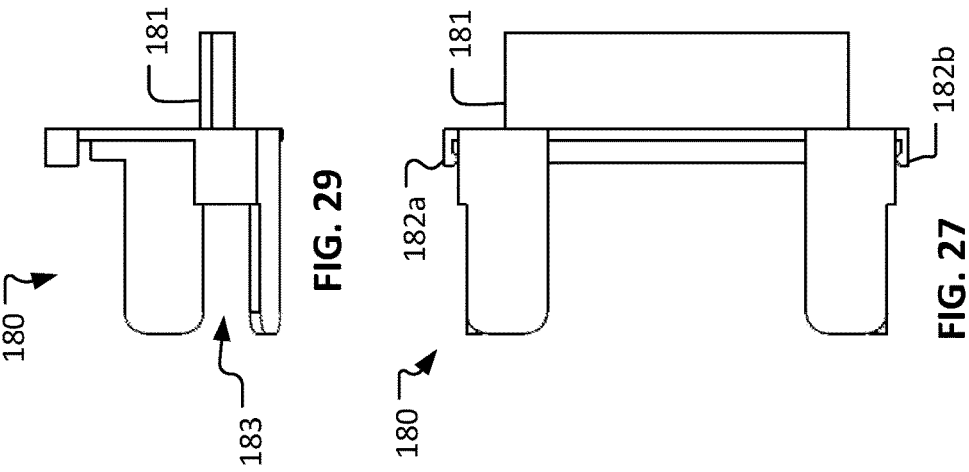
FIG. 29
FIG. 27
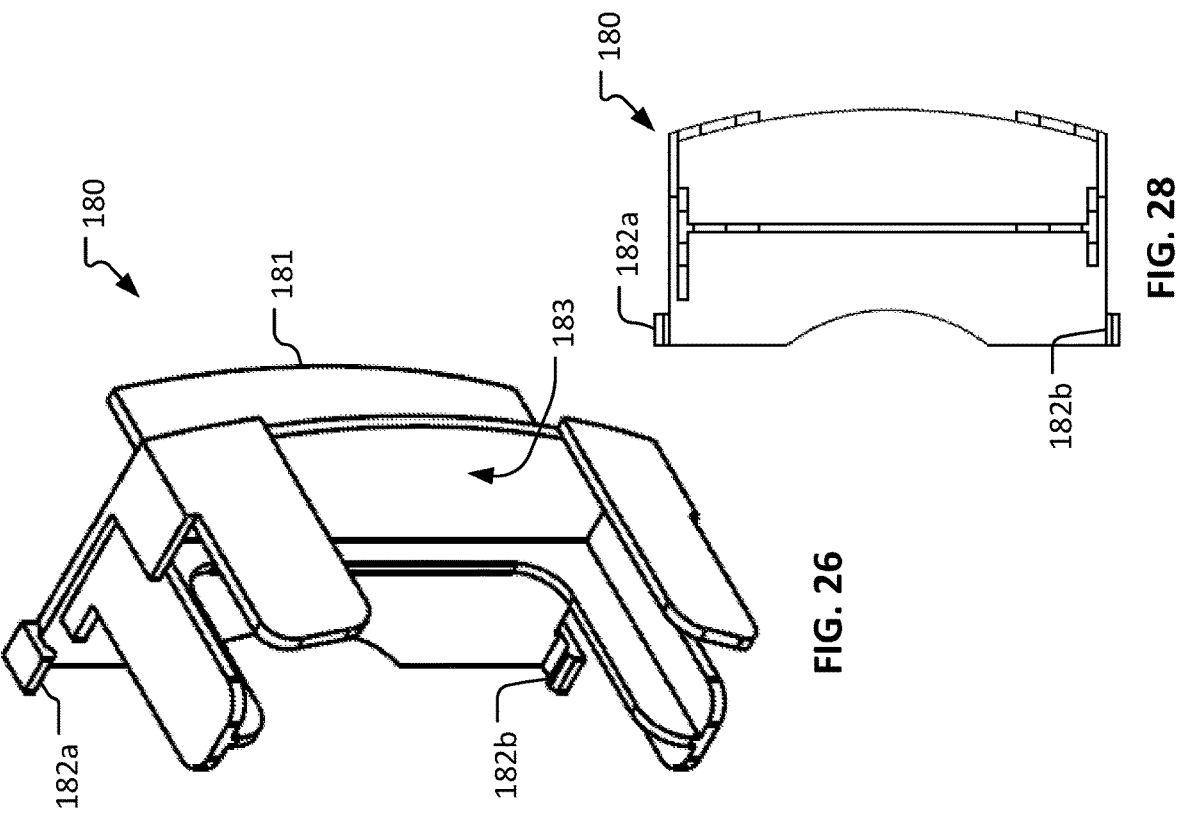
FIG. 26
FIG. 28

111b

100b

170b

170a

140b

100a

170a

111a

52

50a

140b

119a

144b

200

REMOVE COVERS FROM HOME POSITIONS ON
COUPLINGS TO UNCOVER MEMBRANES

210

ENGAGE TWO COUPLINGS TO EACH OTHER IN A FIRST
PRE-COUPLED CONFIGURATION

220

REMOVE MEMBRANES FROM THE COUPLINGS TO
CREATE A SECOND PRE-COUPLED CONFIGURATION

230

REMOVE SPACERS FROM THE COUPLINGS

240

ENGAGE LATCHES TO LOCK THE COUPLINGS TO EACH
OTHER TO CREATE A FINAL COUPLED CONFIGURATION

250

ASEPTIC FLUID COUPLINGS

CROSS-REFERENCE TO RELATED APPLICATIONS

This application is a continuation application of U.S. application Ser. No. 17/122,000 filed on Dec. 15, 2020, which claims the benefit of U.S. Provisional Application Ser. No. 63/045,345 filed Jun. 29, 2020. The disclosure of the prior applications are considered part of (and are incorporated by reference in) the disclosure of this application.

BACKGROUND

1. Technical Field

This document relates to fluid coupling devices for fluid systems and methods. For example, some embodiments described in this document relate to single-use, aseptic fluid coupling devices.

2. Background Information

Some fluid systems, such as some bioprocessing fluid systems or blood handling systems, may require fluid couplings that can aseptically connect a fluid flow path. In one example implementation, it is desirable to connect one or more containers to be able to receive a sample of fluid from a bioreactor system in a manner that prevents contamination of the fluid sample. In that scenario, an aseptic coupling can be used to connect the sample bag(s) to receive the fluid(s) from the bioreactor system while substantially preventing biological contamination of the fluid(s) from the coupling and the environment.

SUMMARY

This document describes fluid coupling devices for fluid systems and methods. In some embodiments, the fluid coupling devices can be implemented as single-use, aseptic fluid coupling connection devices. Some such aseptic couplings are genderless couplings such that two identical aseptic couplings can be coupled together and then latched to form a robust connection between the aseptic couplings.

In particular embodiments, the fluid coupling devices described herein are single-use devices because, after the two portions of the coupling (also referred to herein as "coupling halves" and/or "connectors") are connected to each other, the coupled portions are designed to resist uncoupling. For example, such single-use coupling devices are equipped with one or more mechanical components that operate like locks to maintain the two portions of the coupling in the coupled state. Hence, in these particular embodiments, the fluid coupling devices provided herein are structurally configured to be single-use connection devices so that, after the single-use coupling halves have been connected to each other, they cannot be operably disconnected from each other (as such, preserving the sterility or biological integrity of the system/flow path/etc.).

Further, in such single-use embodiments, or other embodiments, the fluid coupling devices can be configured as genderless couplings. That is, the two coupling portions can be designed exactly alike so that there are no male or female coupling halves as in many conventional fluid coupling designs.

Additionally, in some such single-use embodiments or in other embodiments, the fluid coupling devices can be configured as "aseptic" coupling devices that can be connected to each other while inhibiting biological contamination from migrating into the flow paths. Such an "aseptic" coupling will also serve to limit the exposure of the fluid to the surrounding environment. As used herein, the term "aseptic" refers to any process that maintains a sterilized surface or volume.

As used herein, the term "sterilize" means a process of freeing, to a specified degree, a surface or volume from microorganisms. In example embodiments, the sterility of various components can be achieved using one or more sterilization techniques, including gamma irradiation, E-beam, ethylene oxide (EtO), and/or autoclave technologies.

As used herein, the term "fluid" means any substance that can be made to flow including, but is not limited to, liquids, gases, granular or powdered solids, mixtures or emulsions of two or more fluids, suspensions of solids within liquids or gases, vapors, steam, etc.

In one aspect, this disclosure is directed to an aseptic fluid coupling. The aseptic fluid coupling includes a main body, a seal member, a latch, and a flexible membrane. The main body defines a longitudinal axis, a bore, and a fluid flow path through the main body along the longitudinal axis. The main body includes a front face and a termination that is at an opposite end of the main body relative to the front face. The seal member includes a portion disposed within the bore and a portion extending from the front face around the longitudinal axis. The latch is movably coupled to the main body. The flexible membrane includes a portion attached to the front face around the seal member to block contaminants from entering the fluid flow path. The membrane also includes a tail end portion that is at an opposite end of the membrane in comparison to the portion attached to the front face.

Such an aseptic fluid coupling may optionally include one or more of the following features. The aseptic fluid coupling may be configured for coupling with a second aseptic fluid coupling that is structurally identical to the aseptic fluid coupling. The aseptic fluid coupling may also include a linkage rotatably coupled with the main body and rotatably coupled with the latch. The aseptic fluid coupling may also include a cover attached to the tail end portion of the membrane and rotatably coupled with the main body. The aseptic fluid coupling may also include a cover guide engaged with the cover and the main body. In some embodiments, the cover guide rotatably couples the cover with the main body. The cover may be slidably coupled with the cover guide. The aseptic fluid coupling may also include a spacer disposed between the main body and the latch so as to space the latch apart from the main body. The main body may include two pre-coupling latch members on one side of the main body and two corresponding latch receptacles on an opposite side of the main body. The main body may include a first final latch rib on one side of the main body and a second final latch rib on an opposite side of the main body. The latch may include two first main body latch elements on one side of the latch and two second main body latch elements on an opposite side of the latch. The latch may include a lock member between the first and second main body latch elements.

Particular embodiments of the subject matter described in this document can be implemented to realize one or more of the following advantages. First, in some embodiments, the fluid coupling devices may advantageously provide a user with audible, visual, and/or tactile feedback in reference to the motions performed for physically connecting the two portions of the fluid coupling devices to each other. Such audible and/or tactile feedback can provide the user with an efficient and conclusive indication or confirmation of the proper function and desired configuration of the fluid coupling device.

Second, some embodiments of the fluid coupling devices provided herein are a metallic-free construction (also referred to as a nonmetallic fluid coupling device). As such, such embodiments of the nonmetallic fluid coupling devices can be advantageously sterilized using a gamma sterilization technique. Also, in some circumstances, the nonmetallic fluid coupling devices exhibit enhanced fatigue-resistance characteristics, minimal installed stress, and enhanced corrosion resistance in comparison to some fluid couplings that include traditional metallic parts such as metal springs.

Third, some embodiments of the fluid coupling devices provide an improved aseptic connection capability that may optionally reduce or eliminate the need for sterile rooms or sterile benchtop environments in some cases. As such, these embodiments of the aseptic fluid coupling devices described herein may facilitate efficient and cost-effective operations or uses that would otherwise be high-cost or even cost prohibitive in some traditional settings that required the connection of particular fluid couplings in a sterile room or within a sterile flow-hood to prevent biological contamination.

Fourth, some embodiments of the fluid coupling devices provided herein are advantageously designed to be genderless. Accordingly, usage of the fluid coupling devices are simplified and a user may be able to carry less inventory of fluid coupling components. Also, the genderless aspect of the fluid couplings offers additional system flexibility because anything with one of these couplings can connect to anything else with another one of these couplings.

Fifth, some embodiments of the fluid coupling devices provided herein are advantageously designed with a robust latching system. That is, when two of the couplings are operably connected with each other, they are also mechanically latched or locked together. In some embodiments, once the two couplings are latched together in the operative configuration, the latches are designed to be prevented from being unlatched.

Sixth, the robust latching system of the fluid coupling devices described herein allows for a strong connection between two fluid coupling devices that have large bore sizes, such as about 1 inch to about 1½ inches in diameter, or more.

Unless otherwise defined, all technical and scientific terms used herein have the same meaning as commonly understood by one of ordinary skill in the art to which this disclosure pertains. In addition, the materials, methods, and examples of the embodiments described herein are illustrative only and not intended to be limiting.

The details of one or more embodiments of the invention are set forth in the accompanying drawings and the description herein. Other features, objects, and advantages of the invention will be apparent from the description and drawings, and from the claims.

DESCRIPTION OF THE DRAWINGS

FIGS. 19-22 show various views of a latch of the aseptic coupling of FIG. 2.

FIGS. 23-25 show various views of a linkage of the aseptic coupling of FIG. 2.

FIGS. 26-29 show various views of a spacer of the aseptic coupling of FIG. 2.

Like reference numbers represent corresponding parts throughout.

DETAILED DESCRIPTION OF ILLUSTRATIVE EMBODIMENTS

Figure 1:
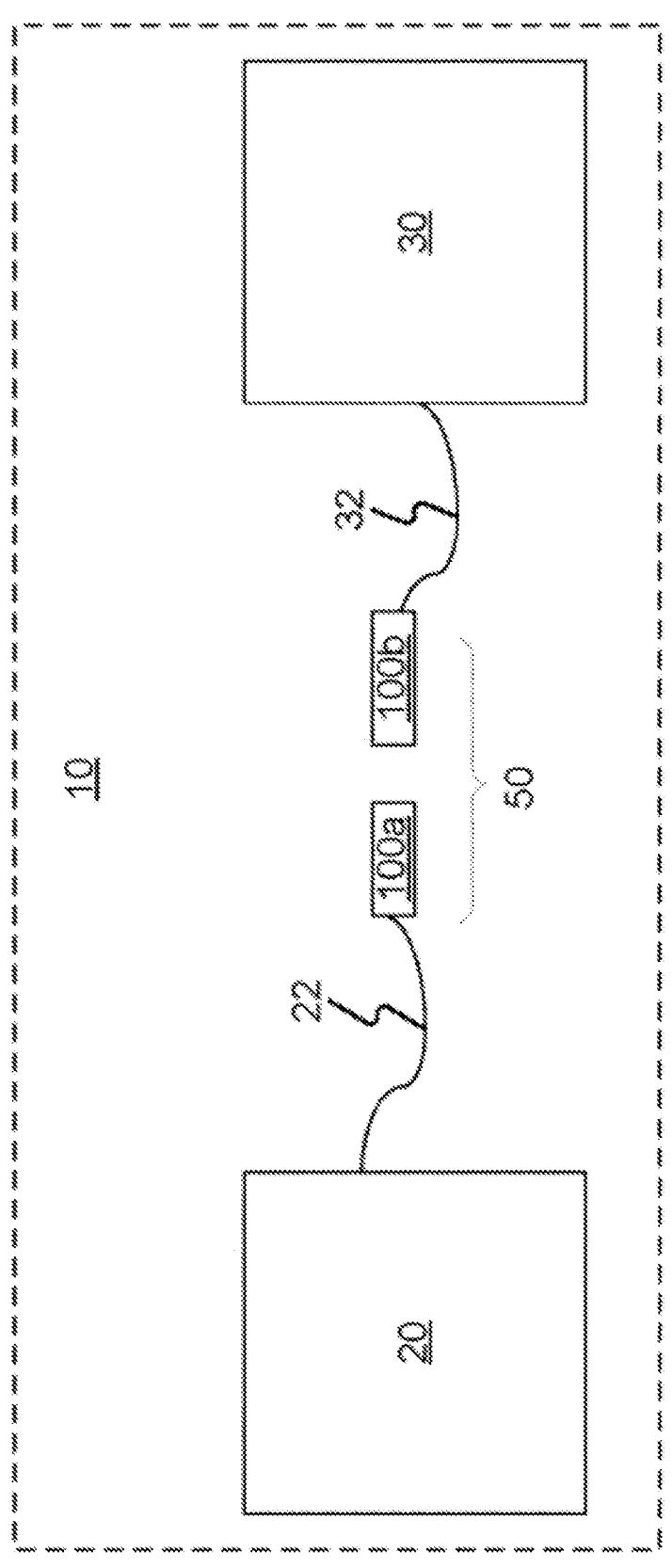
FIG. 1 is a schematic view of an example fluid system including an example fluid coupling arranged in a pre-connected configuration, in accordance with some embodiments provided herein.
Figure 2:
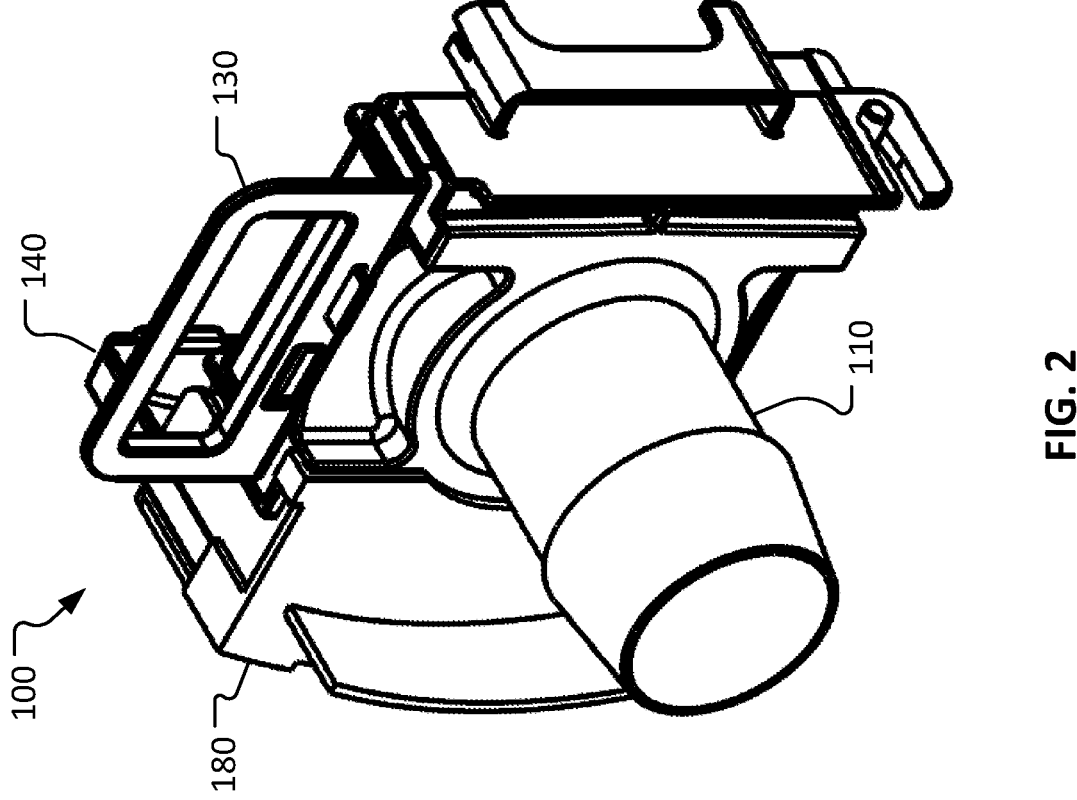
FIG. 2 is a first perspective view of an example aseptic coupling in accordance with some embodiments.
Figure 3:
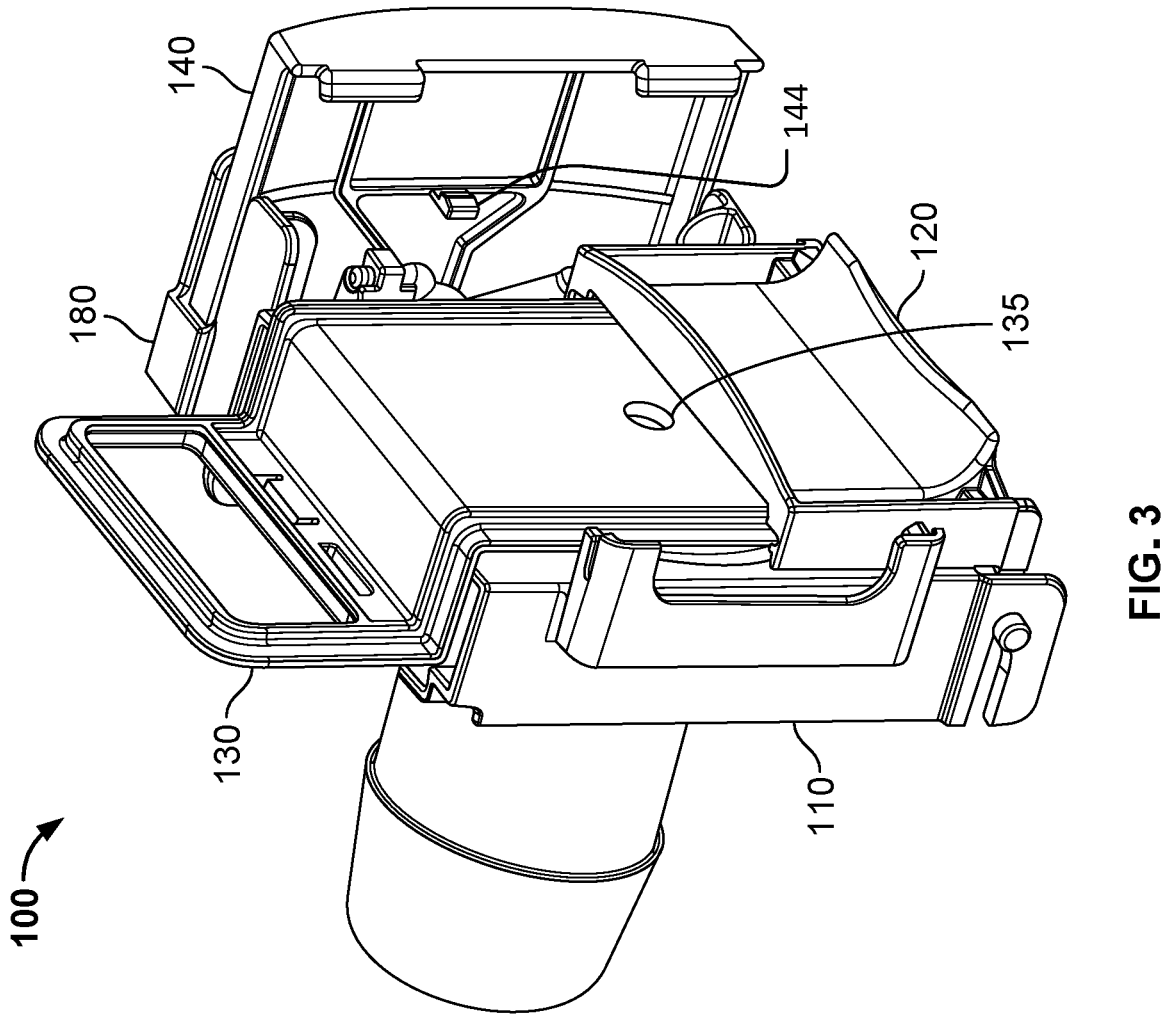
FIG. 3 is a second perspective view of the aseptic coupling of FIG. 2.
Figure 5:
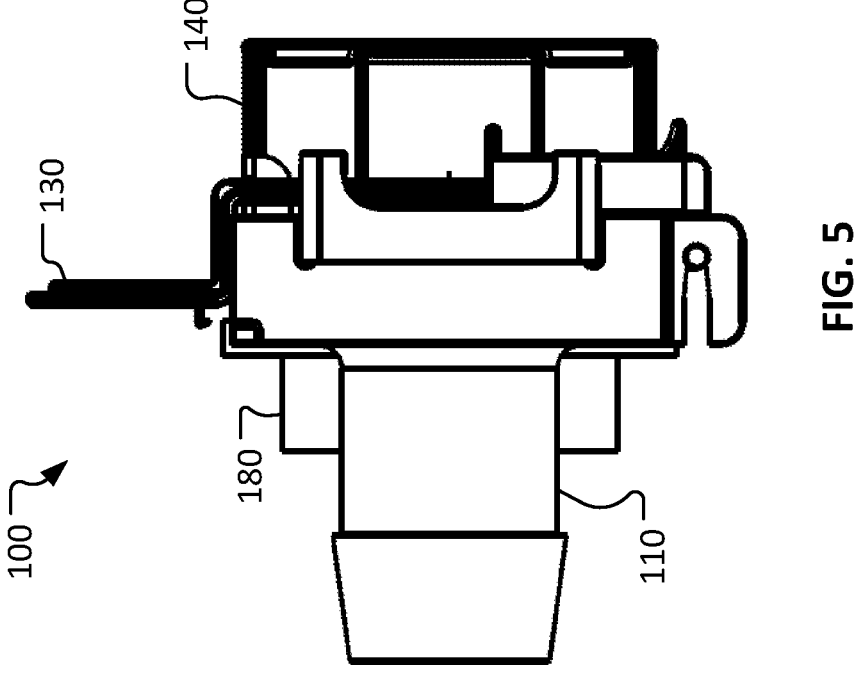
FIG. 5 is a side view of the aseptic coupling of FIG. 2.
Figure 4:
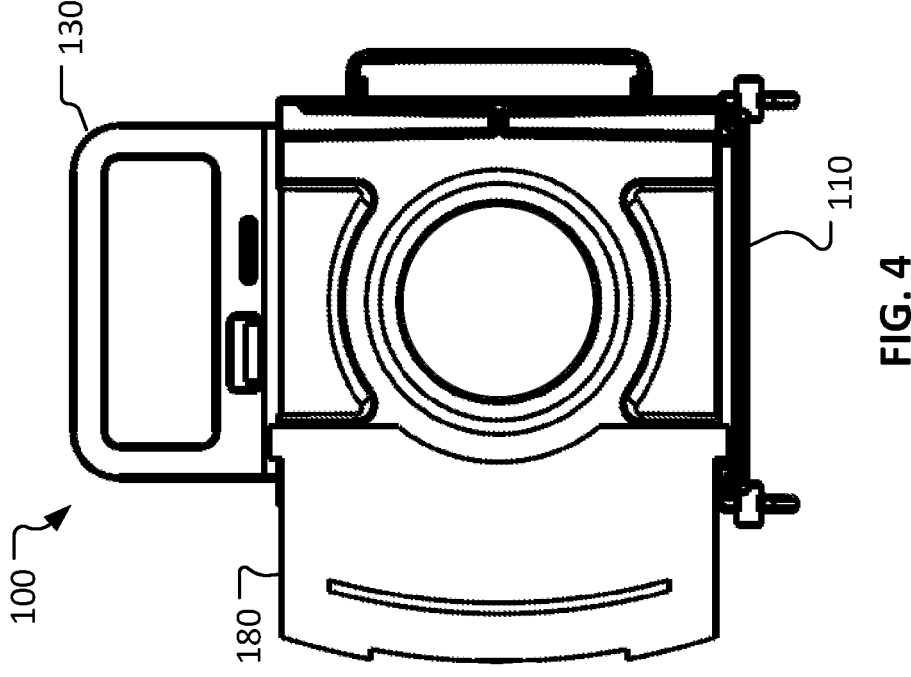
FIG. 4 is a front view of the aseptic coupling of FIG. 2.

Referring now to FIG. 1, an example system 10 is shown. System 10 includes a first piece of processing equipment 20 and a second piece of processing equipment 30. In example embodiments, equipment 20 and 30 are bioreactors including biomaterial. In other embodiments, equipment 20 and 30 can be other apparatuses that require a sterile connection therebetween such as, for example, a bioreactor and a media bag, sample bag, or other receptacle.

Equipment 20 includes a fluid pathway 22 extending therefrom that is terminated by an aseptic coupling arrangement 50 including a first aseptic coupling device 100*a*. Likewise, equipment 30 includes a fluid pathway 32 extending therefrom that is terminated by a second aseptic coupling device 100*b* of the aseptic coupling arrangement 50. The coupling arrangement 50 is representative of the multiple different aseptic couplings described herein.

In example embodiments, aseptic coupling devices 100*a* and 100*b* are substantially similar or genderless (e.g., identical except for possibly differences in terminations). However, it is noted that each aseptic coupling device 100*a*, 100*b* may be provided with different features than the other, as desired.

In example embodiments, the fluid containing environments within pathways 22 and 32 and aseptic coupling devices 100*a* and 100*a* are sterile. In some embodiments, the aseptic coupling arrangement 50 can be placed in an uncoupled configuration, one or more pre-coupled configurations, and in a coupled configuration, as described further below. In a first pre-coupled configuration, while the coupling devices are mechanically coupled to each other, no fluid flow path is open therethrough.

The coupling devices 100*a* and 100*a* are designed and configured so that they can be reconfigured from the uncoupled state to the coupled state (e.g., to connect pathways 22 and 32) while preventing a loss of sterility of the fluid containing environments within the pathways 22 and 32. Hence, using the aseptic coupling arrangement 50, fluid can be transferred between equipment 20 and 30 (via coupling devices 100*a* and 100*a*) without becoming bio-contaminated.

FIGS. 2-6 depict an example aseptic coupling 100. The aseptic coupling 100 is a genderless aseptic coupling. That is, as described below, two of the aseptic couplings 100 can be mated together to create an aseptic coupling arrangement 50 (as shown in FIGS. 31-36) that defines a fluid flow path therethrough. In some cases, at least the internal flow path of the aseptic coupling 100 can be sterile. Accordingly, when two of the aseptic couplings 100 are mated together a sterile flow path through the two mated aseptic couplings 100 can be created.

Figure 6:
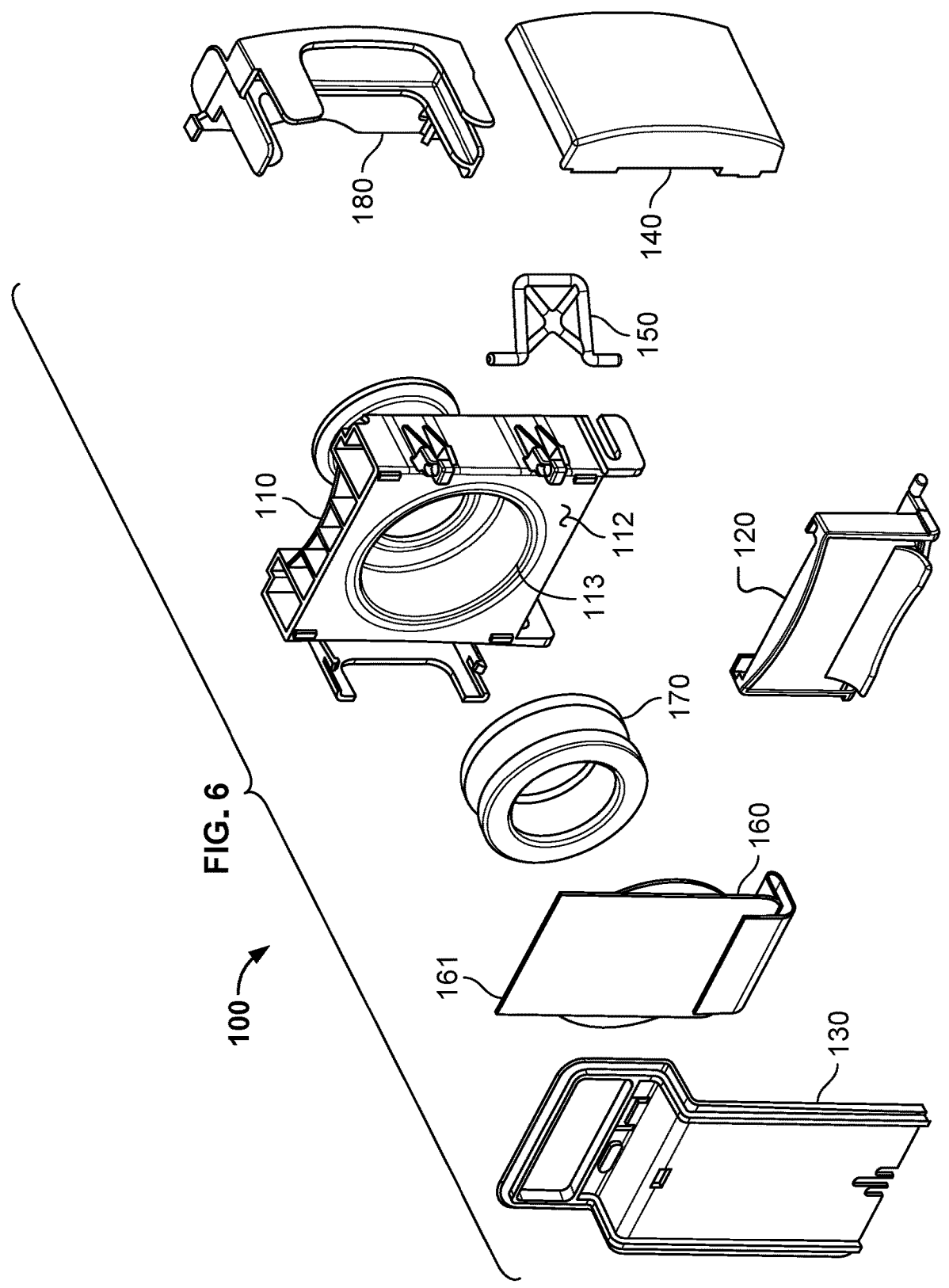
FIG. 6 is an exploded view of the aseptic coupling of FIG. 2.

As best shown in FIG. 6, the aseptic coupling 100 includes a main body 110, a cover guide 120, a cover 130, a latch 140, a linkage 150, a membrane 160, a seal 170, and a spacer 180.

The seal 170 is engaged with the main body 110 in a counter bore defined by the main body 110. A majority of the seal 170 is enclosed within the counter bore, but an end portion of the seal 170 protrudes out from the counter bore, beyond a front face of the main body 110.

The membrane 160 is attached to the front face of the main body 110. The membrane 160 is affixed to the front face circumferentially around the seal 160 so that the membrane 160 covers the seal 160 and the main bore (fluid flow path) of the main body 110.

The cover 130 is affixed to the membrane 160, slidably coupled to the cover guide 120, and latched to the main body 110 (while the cover 130 is in its home position as shown). The cover 130 covers the membrane 160 while the cover is in its home position. The cover 130, which is pivotable in relation to the main body 110, is used as a protector of the membrane 160 (while the cover 130 is in its home position) and as a pulling member to remove the membrane 160 from the main body 110, as described further below.

The cover guide 120, which is an optional component, is pivotably coupled to the main body 110 and slidably coupled to the cover 130. The cover 130 is removable from the cover guide 120, and the cover guide 120 can be removable from the main body 110.

The latch 140 is movably coupled to the main body 110 via the linkage 150. The linkage 150 is pivotably coupled to the main body 110 and also pivotably coupled to the latch 140. The latch 140 is used to firmly compress the aseptic coupling 100 with a second, mated aseptic coupling 100. The latch 140 and the linkage 150 comprise an over-center draw latch that can provide a firm compression of the seals 170 between two coupled aseptic couplings 100, as described further below.

The spacer 180 is slidably engaged with the main body 110 and the latch 140. The spacer 180 holds the latch 140 in a spaced apart orientation with respect to the main body 110 such that two of the aseptic couplings 100 can be mated together in a pre-coupled configuration without interference from the latch 140, as described further below.

The materials from which one or more of the components of the aseptic coupling 100 are made of include thermoplastics. In particular embodiments, the materials from which the components of the aseptic coupling 100 are made of are thermoplastics, such as, but not limited to, acetal, ABS, polycarbonate, polysulfone, polyether ether ketone, polysulphide, polyester, polyvinylidene fluoride (PVDF), polyethylene, polyphenylsulfone (PPSU; e.g., Radel®), polyetherimide (PEI; e.g., Ultem®), polypropylene, polyphenylene, polyaryletherketone, and the like, and combinations thereof. In some embodiments, the components can also include one or more fillers such as glass fiber, glass bead, carbon fiber, talc, etc.

In some embodiments, the materials from which one or more of the components of the aseptic coupling 100 are made of include metals such as, but not limited to stainless steel, brass, aluminum, plated steel, zinc, and the like. In particular embodiments, the aseptic coupling 100 is metallic-free. In some embodiments, non-metallic springs, such as thermoplastic or thermoset can be used in addition to, or as an alternative to, metallic springs/parts.

In certain embodiments, the seal 170 of the aseptic coupling 100 can be made of materials such as, but not limited to, silicone, fluoroelastomers (FKM), ethylene propylene diene monomer (EPDM), thermoplastic elastomers (TPE), buna, buna-N, thermoplastic vulcanizates (TPV), and the like. In some embodiments, the seal 170 has a cross-sectional shape that is an hourglass-shape, an oval shape, a circular shape, a polygonal shape, a multi-lobe shape, D-shaped, X-shaped, square, rectangular, U-shaped, L-shaped, V-shaped, or any other suitable shape, without limitation.

In some embodiments of the seal 170 having an hourglass cross-sectional shape, the seal 170 has a waist portion in the middle of two end portions. The radial thickness of the waist portion is thinner than the two end portions. In some such embodiments, the outer and inner surfaces of the waist portion are arcuate. In such a case, the center of the arc that defines the outer surface of the waist portion is located in an opposite direction in comparison to the center of the arc that defines the internal surface of the waist portion. In some such embodiments, the arc radii of the arc of the outer surface and the arc of the internal surface are unequal. In some such embodiments, the arc radii of the arc of the outer surface and the arc of the internal surface are equal.

The membrane 160 is a thin, flexible member. The membrane 160 can be made of materials such as, but not limited to, polyethersulfone (PES), non-woven polyethylene such as Tyvek®, a PES and polyester laminate, expanded polytetrafluoroethylene (ePTFE), metallic foil, and the like, and combinations thereof. In some embodiments, the membrane 160 is hydrophobic and breathable. In particular embodiments, the pore size of the membrane 160 is such that microorganisms larger than 0.2 microns are filtered out.

Referring to FIGS. 7-10, the main body 110 defines a bore along a longitudinal center axis 2. The bore extends from a termination end 111 to an opposite front face 112. The bore defines a portion of the fluid flow path when two of the aseptic couplings 100 are coupled together in an operative configuration, as described further below.

While the termination end 111 is depicted as a barbed connection, such a fluid connection or termination can be configured in any desired manner (e.g., as a luer fitting, a threaded connection, a Tee fitting, as any type of adapter, a sanitary fitting, etc., without limitation). While the termination end 111 is depicted as being unitary with the other portions of the main body 110, in some embodiments, the termination end 111 can swivel (rotate about the axis 2) in relation to the other portions of the main body 110.

A counter bore 113 (FIG. 6) at the front face 112 makes up a portion of the bore of the main body 110. The counter bore 113 is centered on the axis 2 of the main body 110 and is sized to receive a portion of the seal 170. The other portion of the seal 170 extends beyond the front face 112. Said another way, the depth of the counter bore 113 is less than the length of the seal 170, such that some of the seal 170 stands proud of the front face 112 when the seal 170 is within the counter bore 113.

The front face 112 is the surface to which the membrane 160 is attached. The membrane 160 can be removably coupled to the front face 112 by being bonded (e.g., heat welding, ultrasonic welding, etc.) to the front face 112 such that the membrane 160 covers the seal 170 and the bore of the main body 110. Any suitable bonding technique to removably couple the membrane 204 to the front face surface of the inner member 304 can be used, such as using adhesive.

The main body 110 includes two linkage attachment members 114a and 114b. In the depicted embodiment, the linkage 150 is pivotably coupled to the main body 110 at the linkage attachment members 114a and 114b.

The main body 110 also includes two pre-coupling latch members 115a and 115b. The pre-coupling latch members 115a and 115b are flexible cantilevered members that snap into engagement with corresponding latch receptacles 116a and 116b of a mated aseptic coupling 100. The pre-coupling latch members 115a and 115b latch/detain two aseptic couplings 100 in contact with each other while the aseptic couplings 100 are in the first and second pre-coupled configurations, as described further below.

The main body 110 also includes two final latch ribs 117a and 117b. The final latch ribs 117a and 117b are engaged by the latches 140 of two aseptic couplings 100 that are latched together in the operative coupled configuration, as described further below.

The main body 110 also includes a latch lock structure 119. The latch lock structure 119 is engaged by a lock member 144 (FIGS. 21 and 36) when two aseptic couplings 100 that are latched together in the operative coupled configuration, as described further below.

The main body 110 also includes two cover guide attachment members 118a and 118b. The cover guide attachment members 118a and 118b provide rotatable attachment points for the cover guide 120 to be attached to the main body 110.

Referring to FIGS. 11-14, the cover guide 120 includes two posts 121a and 121b that engage with the cover guide attachment members 118a and 118b of the main body 110 to provide rotatable attachment points for the cover guide 120 to be attached to the main body 110.

The cover guide 120 defines two slots 122a and 122b in which the cover 130 is slidably engaged. The cover 130 is removable from the two slots 122a and 122b as a result of using the cover 130 to remove the membranes 160 from the aseptic couplings 100, as described further below.

The cover guide 120 also includes a grip surface 123. The grip surface 123 can be used by a user to stabilize the aseptic coupling 100 when pulling on the cover 130 to remove the membranes 160 from the aseptic couplings 100, as described further below.

The cover guide 120 is optional. In some embodiments, the aseptic coupling 100 includes no such cover guide 120, and instead the cover 130 is removably attached directly to the main body 110.

Referring to FIGS. 15-18, the cover 130 includes a handle 131 configured for a user to securely grip the cover 130 when pulling on the cover 130 to remove the membranes 160 from the aseptic couplings 100, as described further below.

The cover 130 includes two latch members 132a and 132b. The latch members 132a and 132b engage with complementary structures on the cover guide 120 to keep the cover 130 releasably coupled to the cover guide 120 until a user pulls on the cover 130 to remove the membranes 160 from the aseptic couplings 100, as described further below.

Figures 15, 16, 16A, 17, 18:
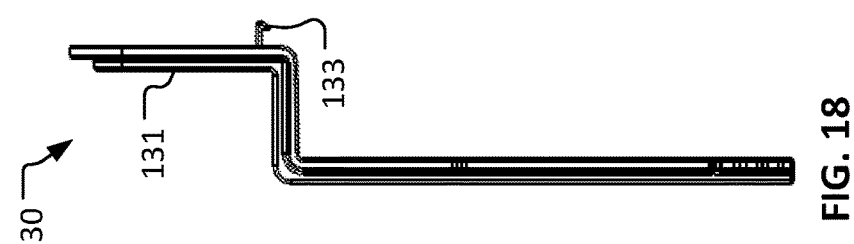
FIGS. 15-18 show various views of a cover of the aseptic coupling of FIG. 2.

FIG. 16a shows an alternative to having the latch members 132a and 132b. That is, instead of the latch members 132a and 132b the cover 130 can include a single latch mechanism 132 is the center of the end portion of the cover 130. In such a case, the cover guide 120 will include a corresponding complementary member sized and positioned to releasably couple with the centered single latch mechanism 132 of the cover 130.

The cover 130 also includes a cover latch member 133 and a cover latch receptacle 134. The cover latch member 133 and the cover latch receptacle 134 are each positioned off-center of the cover 130 and thereby configured for latching together two covers 130 of two aseptic couplings 100 that are configured in the first pre-coupled configuration (FIG. 31), as described further below.

The cover 130 also defines a through-hole 135. The through-hole 135 is positioned to allow gas transfer into and/or out of the bore of the main body 110 (through the membrane 160) when the aseptic coupling 100 is in the uncoupled configuration (e.g., see FIG. 3). This can be beneficial during EtO or steam sterilization of the aseptic coupling 100, for example.

Referring to FIGS. 19-22, the latch 140 includes a linkage attachment structure 141. The linkage attachment structure 141 rotatably couples the latch 140 and the linkage 150.

The latch 140 includes two first main body latch elements 142a and 142b, and two second main body latch elements 143a and 143b. The two first main body latch elements 142a and 142b are used to engage with the final latch rib 117a of a main body 110 of a mated aseptic coupling 100 when two aseptic couplings 100 are in the operable coupled configuration (e.g., FIGS. 35-38). The two second main body latch elements 143a and 143b snap into engagement with the final latch 117b rib of the main body 110 to which the latch 140 is attached to via the linkage 150 when two aseptic couplings 100 are in the operable coupled configuration.

The latch 140 also includes a lock member 144. The lock member 144 is a projection that engages with the latch lock structure 119 of a main body 110 of a mated aseptic coupling 100 when two aseptic couplings 100 are in the operable coupled configuration.

Figures 7, 8, 9, 10:
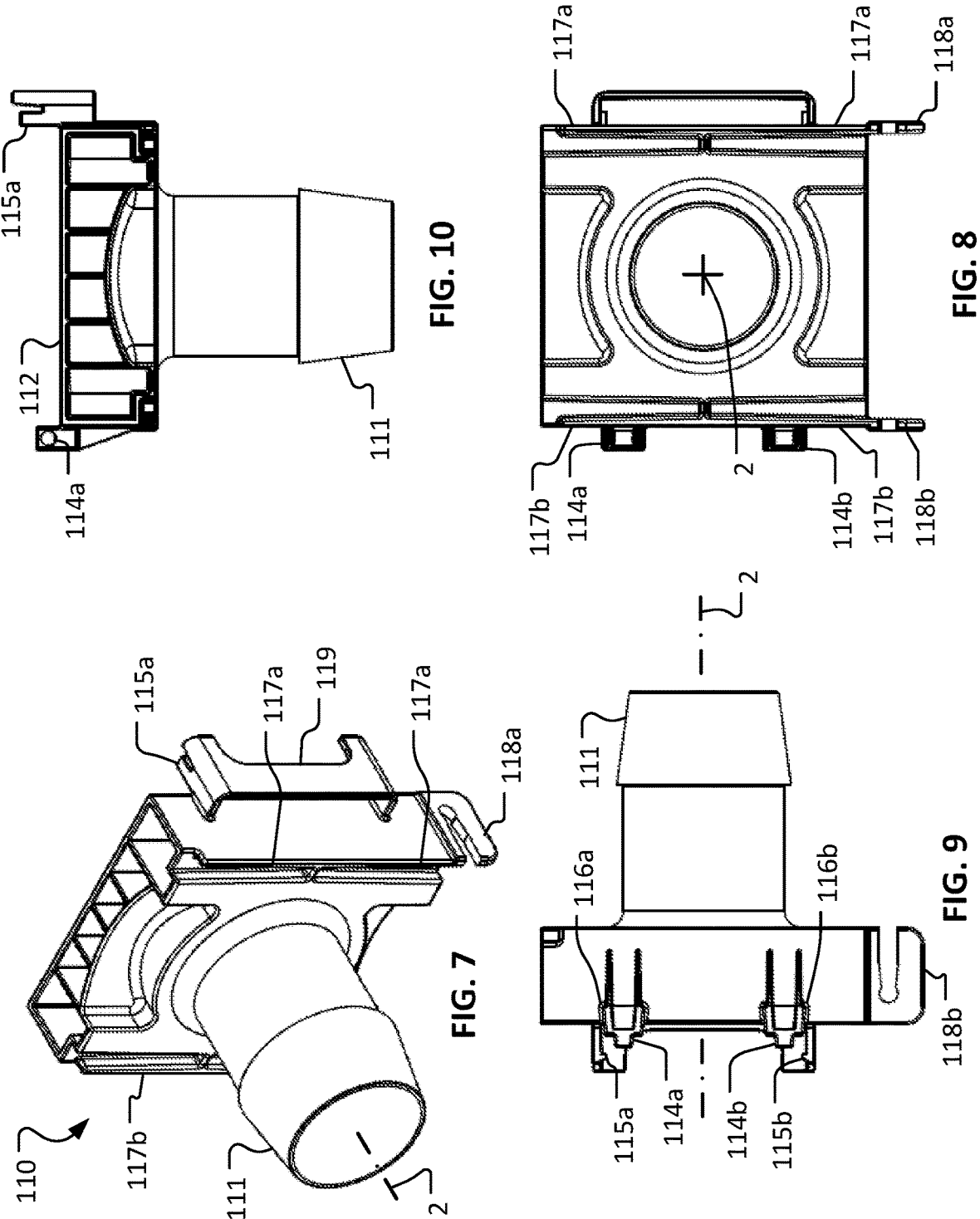
FIGS. 7-10 show various views of a main body of the aseptic coupling of FIG. 2.
Figures 11, 12, 13, 14:
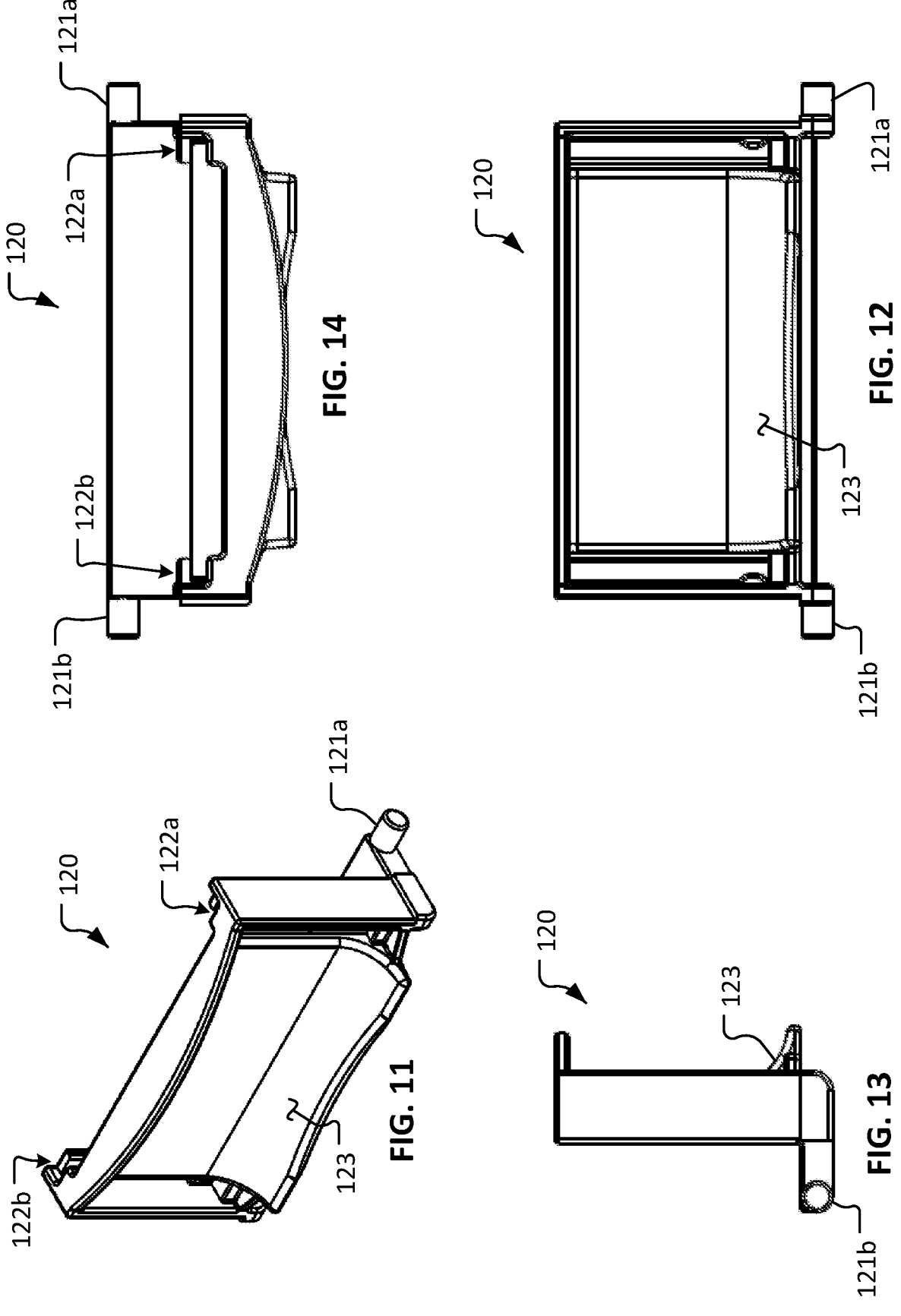
FIGS. 11-14 show various views of a cover guide of the aseptic coupling of FIG. 2.

Referring to FIGS. 23-25, the linkage 150 includes two coupling members 151a and 151b that are rotatably engaged with the linkage attachment members 114a and 114b of the main body 110 (FIGS. 8-10).

The linkage 150 also includes a latch coupling member 152 that is rotatably engaged with the linkage attachment structure 141 of the latch 140 (FIG. 21) to rotatably couple the latch 140 and the linkage 150.

Figures 32, 33:
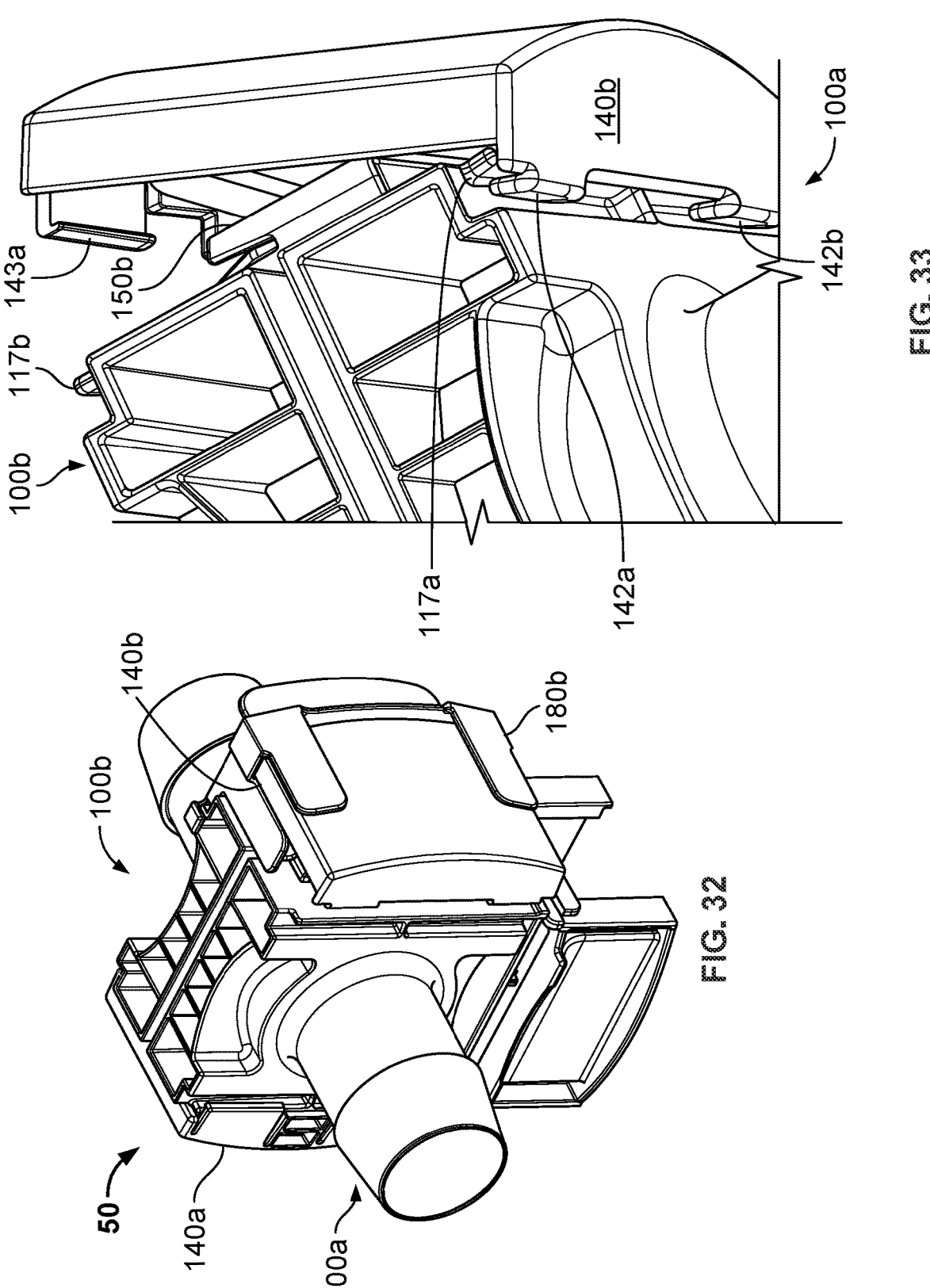
FIG. 32 is a perspective view of two of the aseptic couplings of FIG. 2 engaged together in a second pre-coupled configuration.
FIG. 33 shows the function of the latch of the aseptic coupling of FIG. 2.

Referring to FIGS. 26-29, the spacer 180 includes a handle 181 that a user can grasp onto to pull the spacer 180 away from the other components of the aseptic coupling 100 when two aseptic couplings 100 are in the second pre-coupled configuration (FIG. 32).

The spacer 180 includes two latch members 182a and 182b that releasably engage with the main body 110 to detain the spacer 180 in engagement with the main body 110 until a user intentionally removes the spacer 180 from the other components of the aseptic coupling 100.

The spacer 180 also defines a latch receiving space 183. While the latch 140 resides within the latch receiving space 183, the spacer 180 spaces the latch 140 apart from the main body 110 in a position such that two aseptic couplings 100 can be coupled together to the first and second pre-coupled configurations without interferences from the latches 140.

Figure 30:
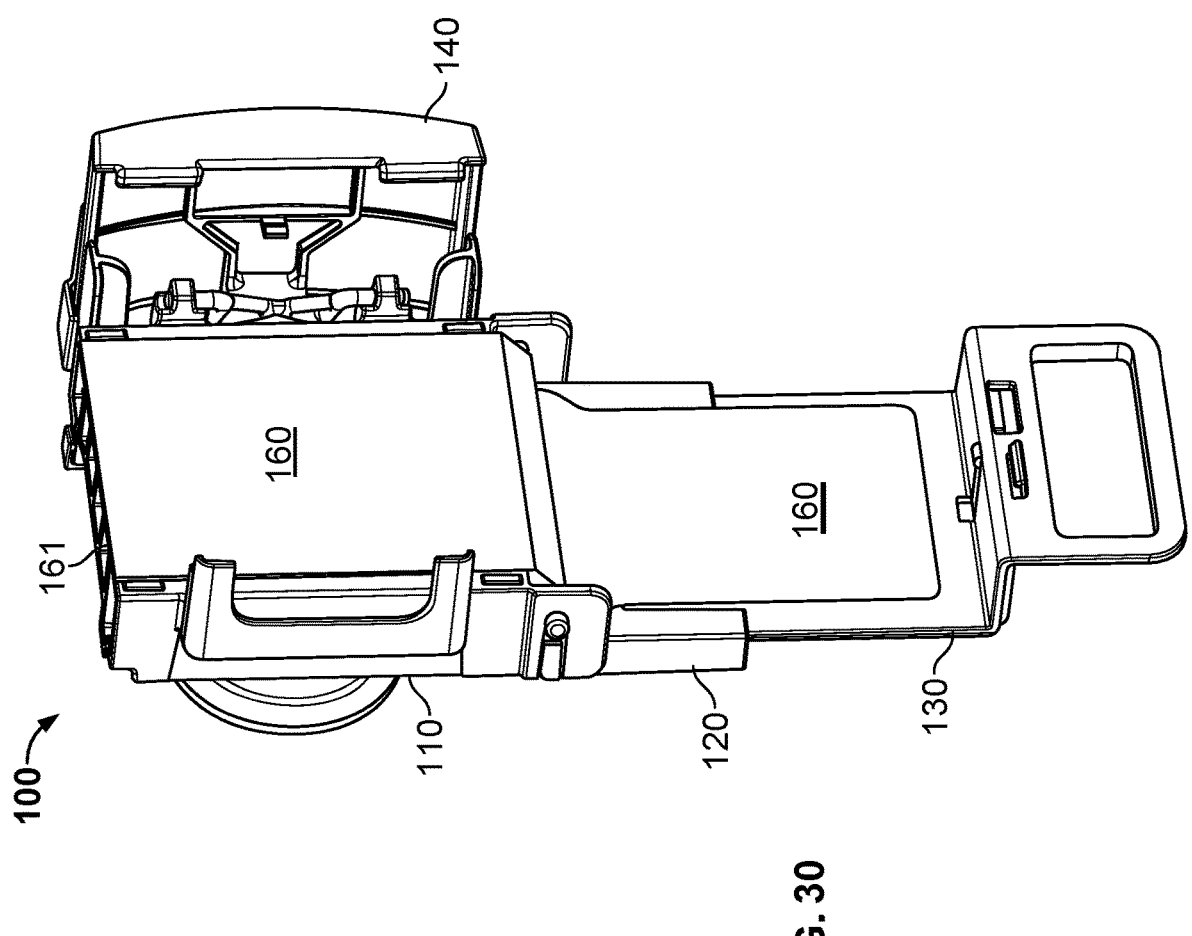
FIG. 30 is a perspective view of the aseptic coupling of FIG. 2 with the cover open in preparation for engaging with a second of the aseptic coupling of FIG. 2.

Referring to FIG. 30, in preparation for coupling the aseptic coupling 100 with another aseptic coupling 100, the cover 130 (and the cover guide 120 if included) and can be pivoted in relation to the main body 110 from its home position (as illustrated in FIGS. 2-5) to the depicted open position in which the membrane 160 is exposed and no longer covered by the cover 130. This configuration of the aseptic coupling 100 is an uncoupled configuration in which the aseptic coupling 100 is configured to be engaged with another aseptic coupling 100. In the depicted position of the cover 130 in relation to the main body 110, the cover 130 (and the cover guide 120 if included) are still removably attached to the main body 110.

The membrane 160 is attached to the cover 130 and to the main body 110. The membrane 160 includes a 180° fold 161. Using the terms "up" and "down" in reference to the depicted orientation of the aseptic coupling 100 (e.g., the cover 130 is located downward from the main body 110), the membrane 160 is orientated as follows. The membrane 160 is removably attached to the front face 112 of the main body 110 (FIG. 6). More particularly, the membrane 160 is attached to the front face 112 circularly (annularly) around the seal 170 so as to cover and isolate the seal 170 (and bore of the main body 110) from ambient exposure. Accordingly, the membrane 160 maintains the sterility of the seal 170 and bore of the main body 110. The membrane 160 may also be attached to the front face 112 linearly along an upper edge of the front face 112 of the main body 110. From the membrane's attachment location(s) on the front face 112, the membrane 160 extends upward towards the fold 161. The membrane 160 makes a 180° turn at the fold 161, and then extends down toward the cover 130. The end portion of the membrane 160 is affixed to the cover 130. The end portion of the membrane 160 can be affixed on either side of the cover 130 (e.g., to the "front" side as shown in FIG. 30, or to the opposite/"back" side of the cover 130). Accordingly, when the cover 130 is manually pulled downward (as described further below), the fold 161 will progress/roll downward and the membrane 160 will peel off from the front face 112.

Figure 31:
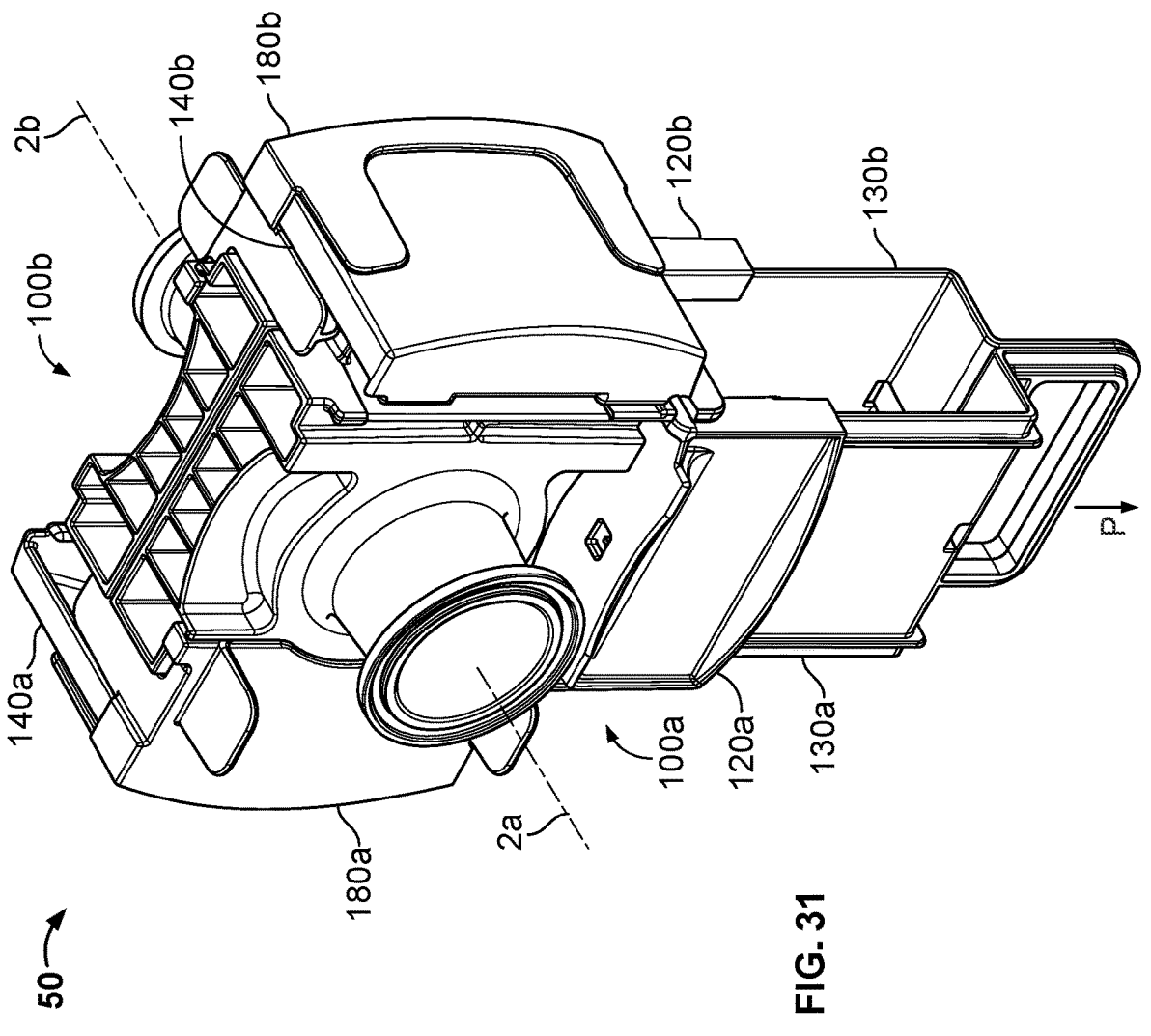
FIG. 31 is a perspective view of two of the aseptic couplings of FIG. 2 engaged together in a first pre-coupled configuration.

FIG. 31 depicts an aseptic coupling arrangement 50 in a first pre-coupled configuration. The aseptic coupling arrangement 50 includes a first aseptic coupling 100a and a second aseptic coupling 100b. In particular, the first aseptic coupling 100a and the second aseptic coupling 100b are coupled to each other, but the respective membranes 160a-b of the aseptic couplings 100a-b are still attached. Accordingly, no fluid flow path through the aseptic coupling arrangement 50 has yet been opened.

In the first pre-coupled configuration as shown, the seals 170a-b (not visible, FIG. 6) compress or sandwich the two membranes 160a-b between the seals 170a-b. In fact, because of the folds 161a-b in the membranes 160a-b, there are four layers of the membranes 160a-b compressed between the two seals 170a-b (because each membrane 160a-b is doubled over on itself).

When the two aseptic couplings 100a-b are mated together in the first pre-coupled configuration as shown, the main bodies 110a-b of the two aseptic couplings 100a-b are latched together. In particular, the two pre-coupling latch members 115a and 115b (FIG. 9) of the main body 110a are latched with the latch receptacles 116a and 116b of the main body 110b. In addition, the two pre-coupling latch members 115a and 115b of the main body 110b are latched with the latch receptacles 116a and 116b of the main body 110a.

In addition, when the two aseptic couplings 100a-b are mated together in the first pre-coupled configuration as shown, the covers 130a-b can be latched together. That is, the cover latch member 133 of the first cover 130a can be latched with the cover latch receptacle 134 of the second cover 130b. In addition, the cover latch member 133 of the second cover 130b can be latched with the cover latch receptacle 134 of the first cover 130a.

The membranes 160a-b can be removed from the pre-coupled aseptic couplings 100a-b by pulling on the covers 130a-b. That is, a user can manually grasp the covers 130a-b (e.g., grasping both handles 131a-b simultaneously) and simultaneously pull on the covers 130a-b transversely away from the longitudinal axes 2 of the two aseptic couplings 100a-b as indicated by arrow P. Since the covers 130a-b can be latched to each other, pulling simultaneously is facilitated. Pulling the membranes 160a-b transversely away from the longitudinal axes 2a-b of the two aseptic couplings 100a-b will cause the folds 161a-b (FIG. 30) to progress in the transverse direction of the pulling P by rolling. As the folds 161a-b progress transversely to the axes 2a-b in that manner, the membranes 160a-b are being removed from the front faces 112a-b (FIG. 6) of the two aseptic couplings 100a-b. As the membranes 160a-b are removed from the front faces 112a-b, the seals 170a-b eventually make contact with each other and a sterile flow path through the aseptic coupling arrangement 50 is created. The rolling of the membranes 160a-b helps ensure that no exterior surface of the membranes 160a-b ever contacts the seals 170a-b, and therefore sterility of the flow path areas of the aseptic couplings 100a-b is maintained as the membranes 160a-b are removed.

Once the membranes 160a-b are removed, the aseptic couplings 100a-b are in the second pre-coupled configuration wherein the seals 170a-b are in contact with each other and a sterile flow path through the aseptic coupling arrangement 50 is created. However, it can be beneficial to thereafter clamp the aseptic couplings 100a-b together with more force and security than what is provided by the two pre-coupling latch members 115a and 115b (FIG. 9) that are latched with the latch receptacles 116a and 116b. In fact, the compression between the seals 170a-b that is provided by the two pre-coupling latch members 115a and 115b that are latched with the latch receptacles 116a and 116b is purposely limited so that the membranes 160a-b can be manually pulled out without excessive force. Thereafter, it can be desirable to increase that compression between the seals 170a-b to ensure leak-proof operation and robust mechanical connection between the aseptic couplings 100a-b. Moreover, that is especially true with increasing sizes of the aseptic couplings 100a-b.

As described further below, the latches 140a-b are used to clamp the aseptic couplings 100a-b together with a degree of compression between the seals 170a-b that ensures leak-proof operation and a robust mechanical connection between the aseptic couplings 100a-b.

FIG. 32 shows aseptic coupling arrangement 50 in the process of becoming clamped together using the latches 140a-b. In particular, the latch 140a is fully clamping its side of the aseptic couplings 100a-b together, but the latch 140b has not yet been activated into operation. In fact, the spacer 180b is still in place. Therefore, the reconfiguration of the aseptic coupling arrangement 50 from the second pre-coupled configuration to the final operative configuration is not yet fully complete in the arrangement of FIG. 32.

FIG. 33 shows the latch 140b in the process of being activated into operation (i.e., to clamps its sides of the aseptic couplings 100a-b together). The spacer 180b has been removed. Then, a user can manually manipulate the latch 140b to engage the latch's two first main body latch elements 142a and 142b with the final latch rib 117a of the aseptic coupling 100a. The linkage 150b facilitates those motions.

Figure 34:
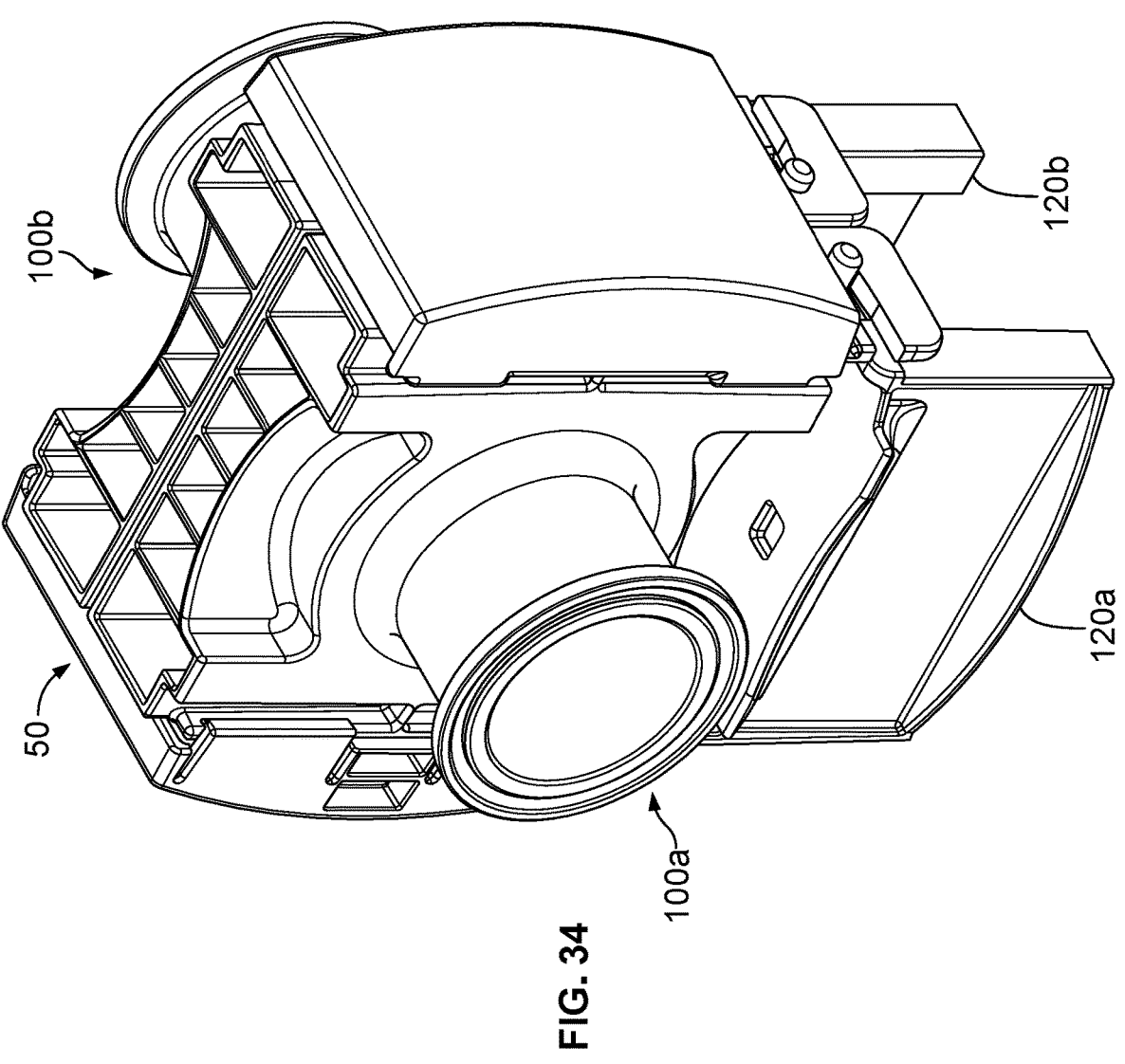
FIG. 34 is a perspective view of two of the aseptic couplings of FIG. 2 engaged together in an operative coupled configuration.

Then, while the two first main body latch elements 142a and 142b are engaged with the final latch rib 117a as shown, the end of the latch 140b where the two second main body latch elements 143a and 143b (not visible) are located can be manually pressed toward the aseptic coupling 100b. In doing so, the latch 140b will naturally snap into its final position (as shown in FIG. 34) in which the two second main body latch elements 143a and 143b are engaged with the final latch rib 117b of the aseptic coupling 100b.

It can be envisioned that the latch 140b and the linkage 150b are design to act as an over-center latch. This over-center latch design (including both latches 140a-b of the aseptic coupling arrangement 50) robustly draws the two aseptic couplings 100a-b together and latches them together while also compressing the two seals 170a-b together firmly to ensure a leak-proof seal. For example, the length of the latch 140b from center-to-center of the pivot points is less than the distance between the contact points on the mating parts.

Figures 35, 36:
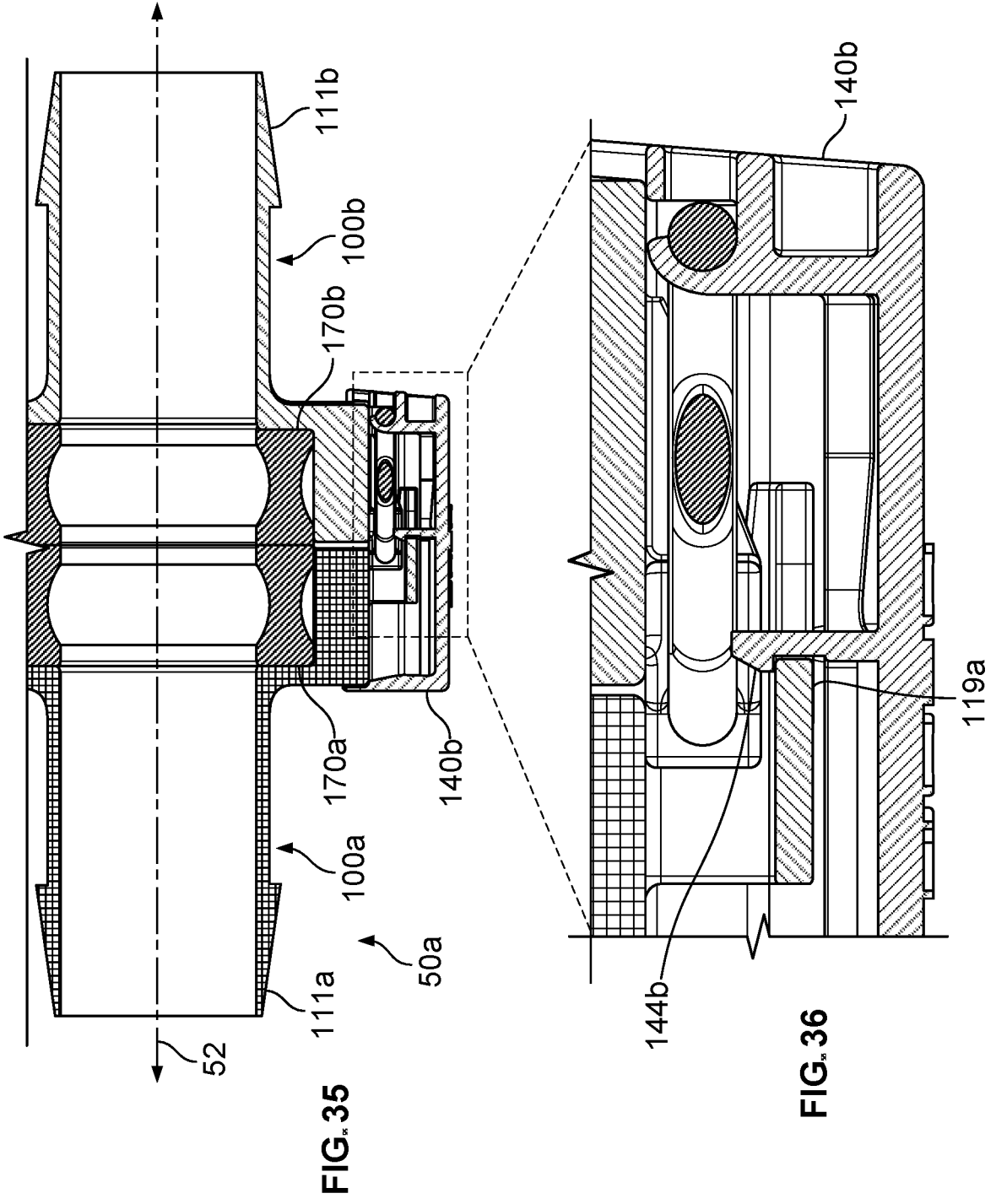
FIG. 35 is a longitudinal cross-sectional view of a portion of two of the aseptic couplings of FIG. 2 engaged together in an operative coupled configuration.
FIG. 36 is an enlarged view of a portion of FIG. 35.

Referring to FIGS. 35 and 36, in the operative coupled configuration, the aseptic coupling arrangement 50 defines an open fluid flow path 52 through the bores and the seals 170a-b of the aseptic couplings 100a-b. The front faces of the seals 170a-b are compressed together.

In some embodiments, the aseptic coupling devices 100a-b are single-use devices because, after the aseptic coupling devices 100a-b are fully connected to each other in the operative coupled configuration, the aseptic coupling devices 100a-b are designed to resist uncoupling. For example, some such single-use coupling devices are equipped with one or more mechanical components that operate like locks to maintain the aseptic coupling devices 100a-b in the coupled state. Hence, in these particular embodiments, the aseptic coupling devices 100a-b are structurally configured to be single-use connection devices so that, after the single-use aseptic coupling devices 100a-b have been connected to each other, they cannot be operably disconnected from each other (as such, preserving the sterility or biological integrity of the system/flow path/etc.).

As best seen in FIG. 36, the mechanical components that operate like locks to maintain the aseptic coupling devices 100a-b in the coupled state include the lock member 144b on the latch 140b (and the lock member 144a on the latch 140a, not visible). The lock member 144b engages with the latch lock structure 119a on the main body 110a (FIG. 7) of the aseptic coupling 100a when the latch 140b is snapped into its final latched position. Accordingly, the lock member 144b and the latch lock structure 119a resist reopening of the latch 140b.

Figure 37:
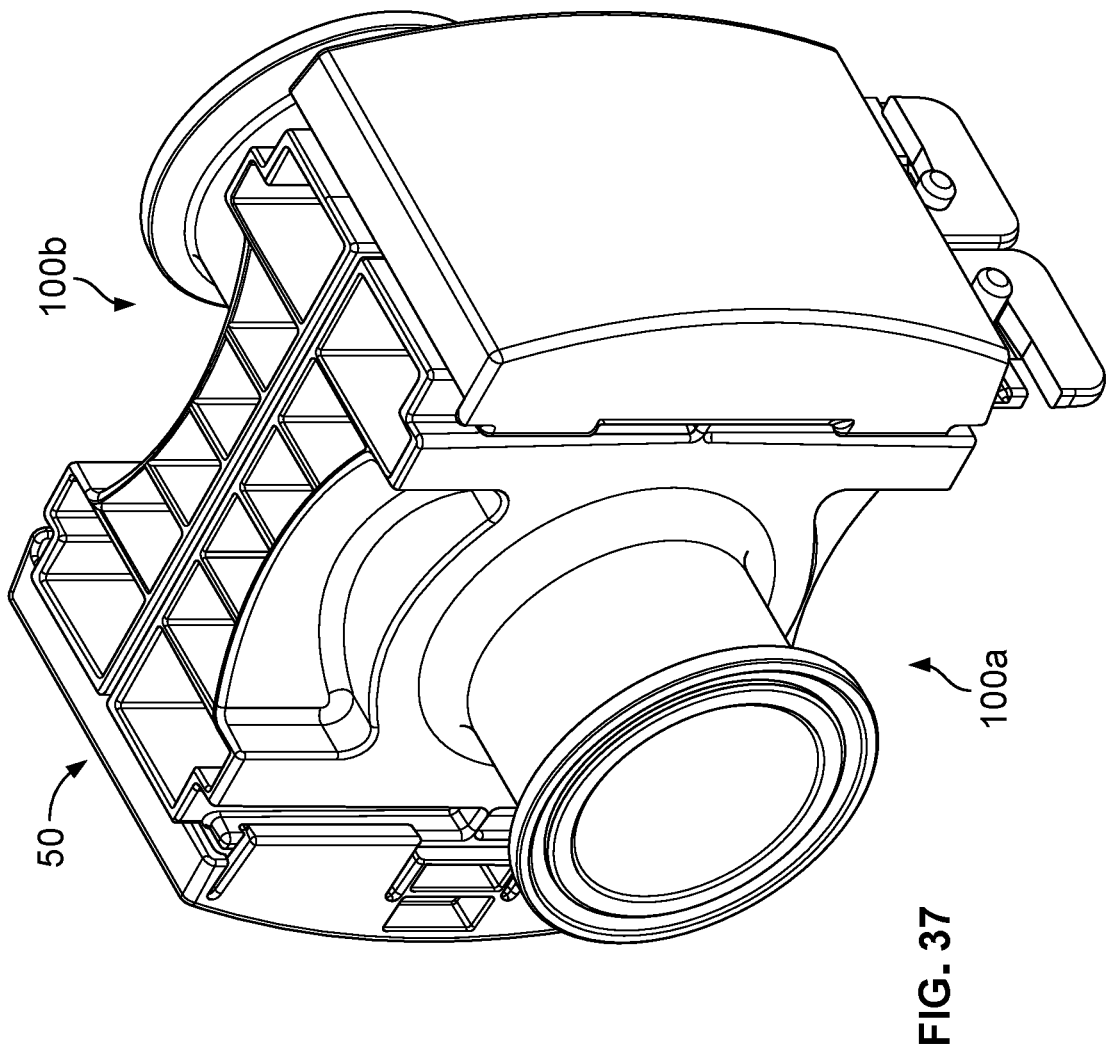
FIG. 37 is a perspective view of two of the aseptic couplings of FIG. 2 engaged together in another operative coupled configuration.

Referring to FIG. 37, if the user so chooses, the aseptic coupling arrangement 50 can be used with the cover guides 120 (FIG. 34) removed. Or, if the user so chooses, the aseptic coupling arrangement 50 can be used with the cover guides 120 still attached (FIG. 34).

Figure 38:
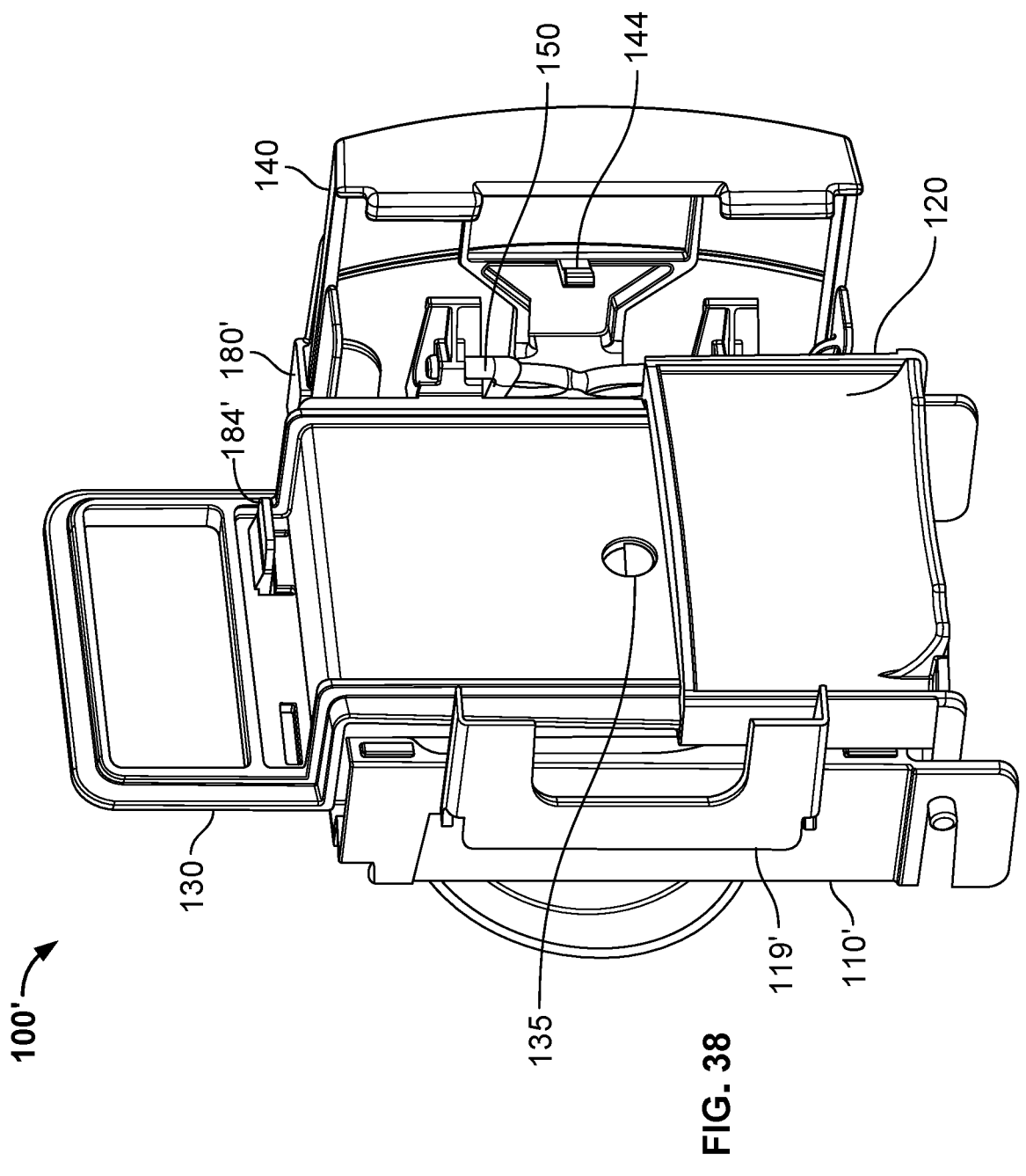
FIG. 38 is a perspective view of another example aseptic coupling in accordance with some embodiments.

Referring to FIG. 38, another example aseptic coupling device embodiment is depicted. This aseptic coupling device 100' shares most of the features of the aseptic coupling device 100 described above, but some differences exist between the aseptic coupling device 100' and the aseptic coupling device 100, as described further below. It should be understood that the features of the aseptic coupling device 100' and the aseptic coupling device 100 can be combined in any desired combination to create hybrid embodiments of the aseptic coupling device embodiments described herein.

The aseptic coupling device 100' includes a main body 110', the cover guide 120 (as described above), the cover 130 (as described above), the latch 140 (as described above), the linkage 150 (as described above), a membrane 160 (not visible; as described above), a seal 170 (not visible; as described above), and a spacer 180'. These component parts of the aseptic coupling device 100' are related to each other as described above in reference to the aseptic coupling device 100.

Figures 39, 40:
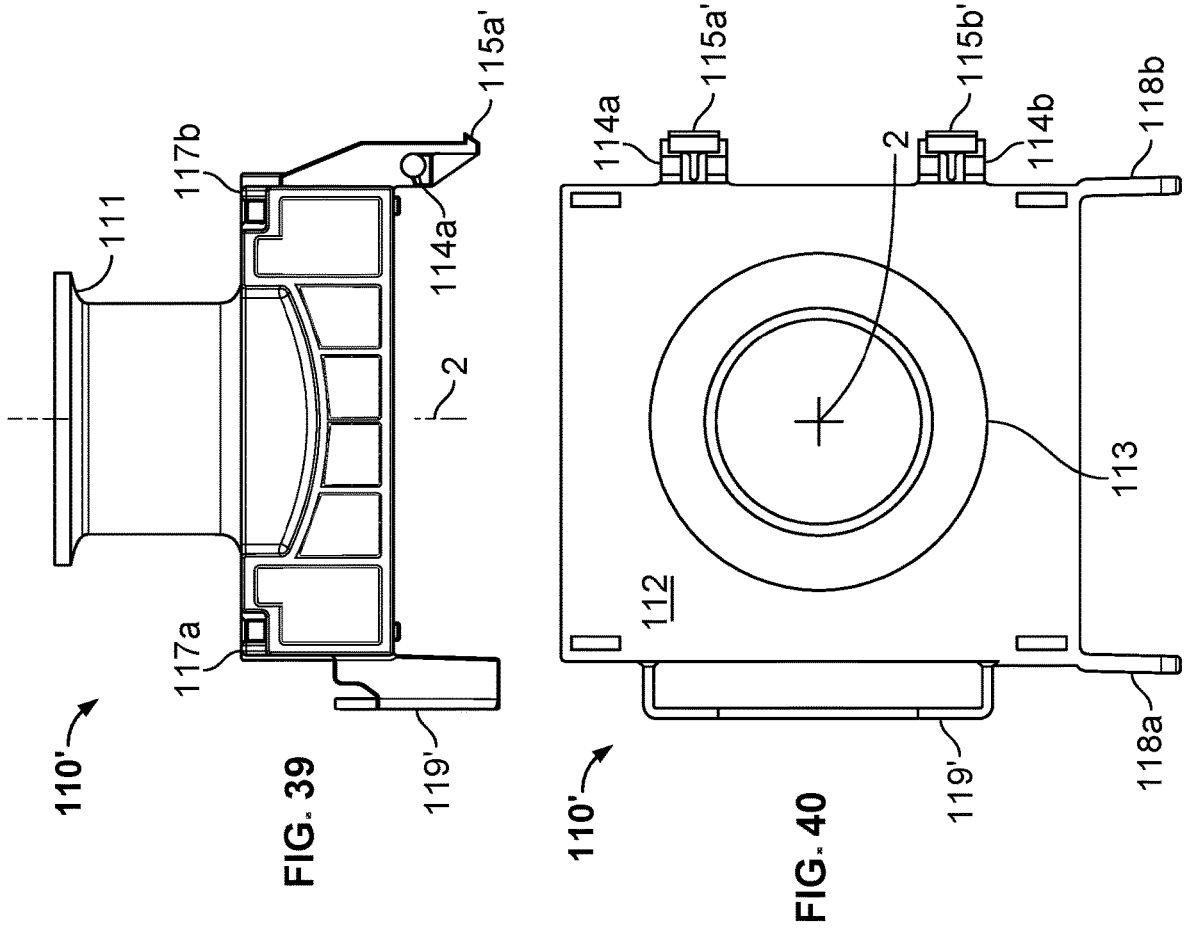
FIGS. 39 and 40 show a top and end view of a main body of the aseptic coupling of FIG. 38.

Referring to FIGS. 39 and 40, the main body 110' is shown in isolation so that its unique features are more visible. The unique features (in comparison to the main body 110 described above) include the two pre-coupling latch members 115a' and 115b' and the latch lock structure 119'.

The pre-coupling latch members 115a' and 115b' are barbed cantilevered projections that snap into engagement with a corresponding latch lock structure 119' of a mated aseptic coupling 100'. This engagement can be seen in FIG. 42. In some embodiments, the pre-coupling latch members 115a' and 115b' are more rigid than the latch lock structure 119' such that the latch lock structure 119' flexes outwardly as the pre-coupling latch members 115a' and 115b' slide into latched engagement with the latch lock structure 119'.

Figure 41:
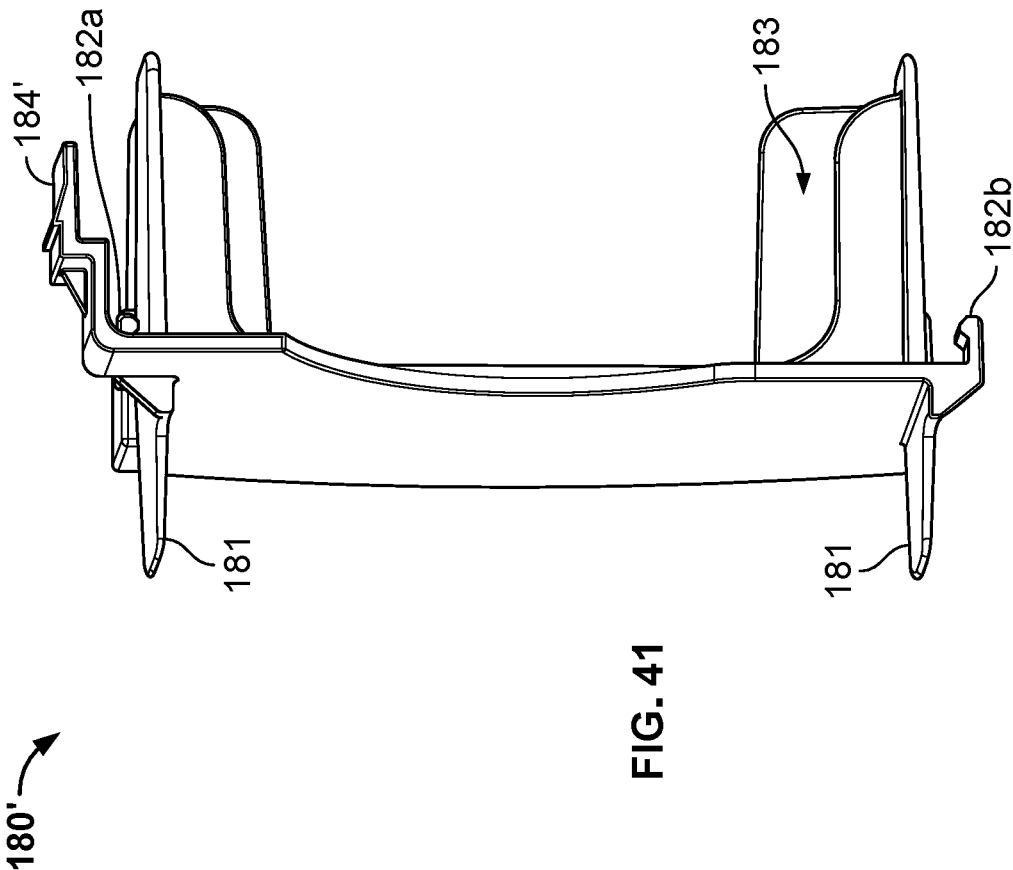
FIG. 41 is a perspective view of a spacer of the aseptic coupling of FIG. 38.

FIG. 41 shows the spacer 180' in isolation so that its unique features are more visible. The unique features (in comparison to the spacer 180 described above) include a cantilevered latch member 184'. The cantilevered latch member 184' releasably latches with the cover 130 when the cover 130 is in its home position (as shown in FIG. 38). This engagement between the spacer 180' and the cover 130 (via the cantilevered latch member 184') releasably detains the cover 130 in its home position prior to the beginning of the process of coupling the aseptic coupling device 100' to another aseptic coupling device 100'.

Similar to as described above, to begin the process of coupling the aseptic coupling device 100' to another aseptic coupling device 100', the covers 130 need to be pivoted in relation to the main body 110' away from the home positions of the covers 130. As a result of that pivoting, the covers 130 hang down and the membranes 160 become exposed (as depicted in FIG. 30, for example). In order to pivot the cover 130, the latched engagement between the spacer 180' and the cover 130 (via the cantilevered latch member 184') must first be disengaged. To do so, a user can depress the free end portion of the cantilevered latch member 184' to deflect the barb end portion of the cantilevered latch member 184' out of engagement from the cover 130 (e.g., see FIG. 38). Then, while the cantilevered latch member 184' is held in its deflected position, the cover 130, which is no longer latched to the spacer 180', can be pivoted away from its home position.

Figure 42:
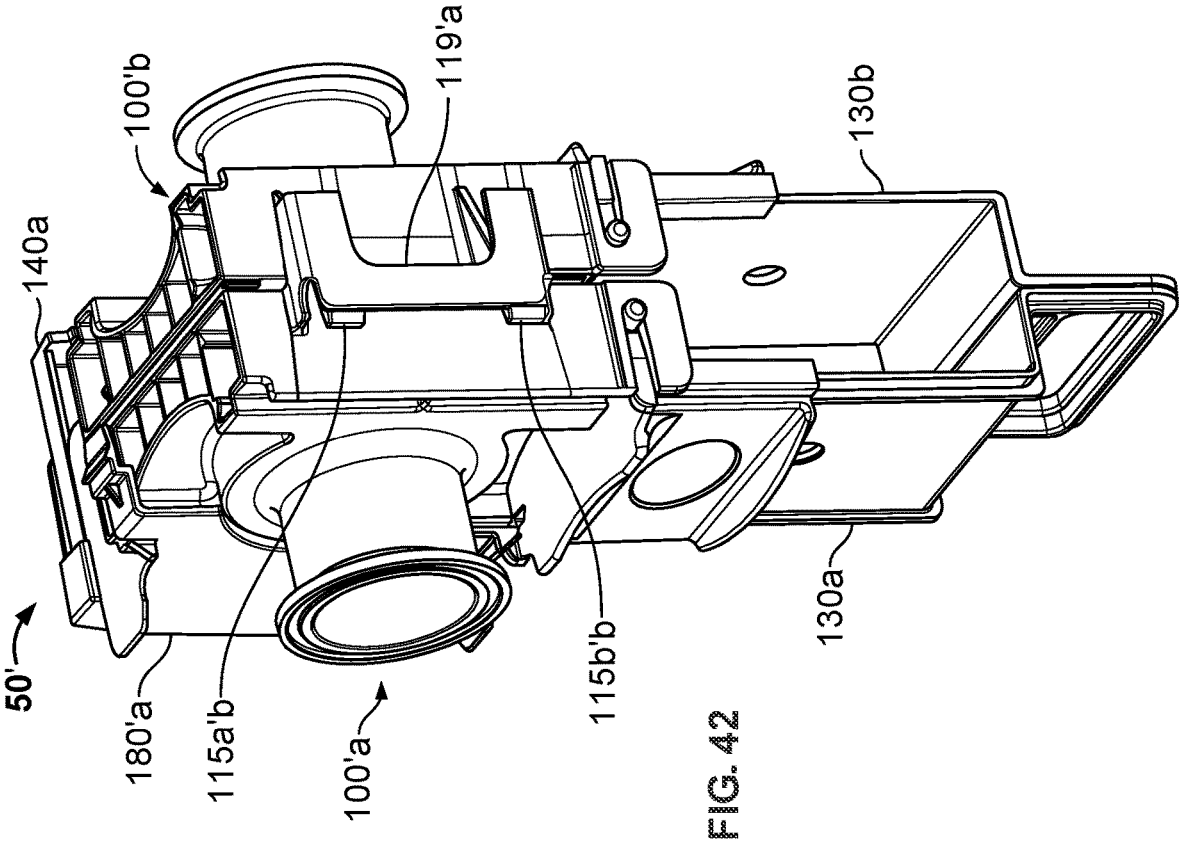
FIG. 42 is a perspective view of two of the aseptic couplings of FIG. 38 engaged together in a first pre-coupled configuration.

FIG. 42 depicts an aseptic coupling arrangement 50' in a first pre-coupled configuration. The aseptic coupling arrangement 50' includes a first aseptic coupling 100a' and a second aseptic coupling 100b'. In particular, the first aseptic coupling 100a' and the second aseptic coupling 100b' are coupled to each other, but the respective covers 130a-b (and the associated membranes 160a-b, not visible) of the aseptic couplings 100a'-b' are still attached. Accordingly, no fluid flow path through the aseptic coupling arrangement 50' has yet been opened.

In the first pre-coupled configuration of the aseptic coupling arrangement 50' as shown, it can be seen that the two pre-coupling latch members 115a'b and 115b'b of the second aseptic coupling 100b' are latched with the latch lock structure 119'a of the first aseptic coupling 100a'. In this illustration, the latch 140b, linkage 150b, and the spacer 180' are not shown so that the area of the two pre-coupling latch members 115a'b and 115b'b and the latch lock structure 119'a are clearly visible.

The remaining steps for completing the coupling process between the first aseptic coupling 100a' and the second aseptic coupling 100b' are as described above in reference to FIGS. 31-36.

Figure 43:
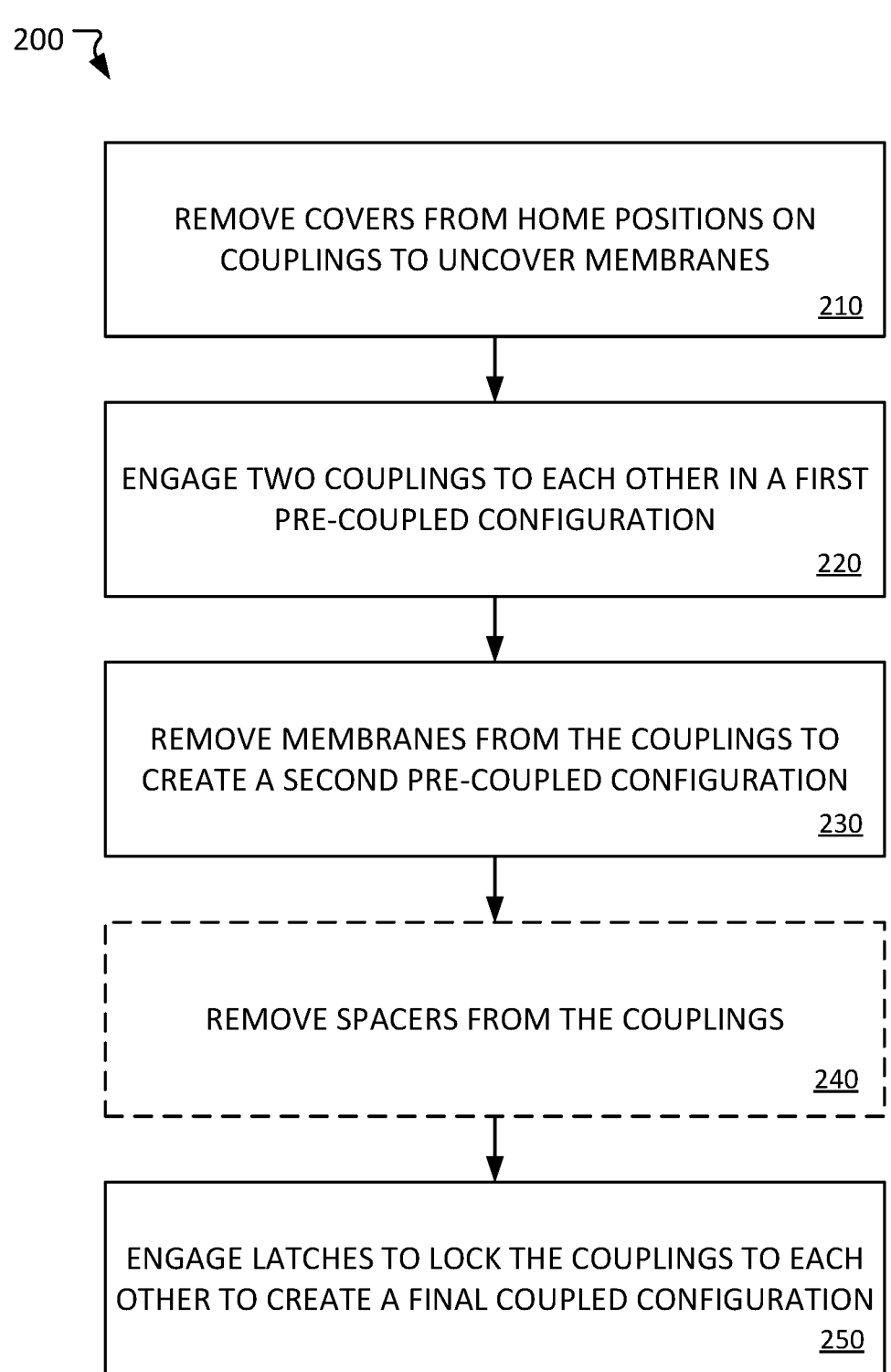
FIG. 43 is a flowchart of an example method of creating an aseptic coupling between two aseptic coupling devices as described herein.

FIG. 43 illustrates a method 200 of creating an aseptic coupling for use, for example, in a system 10 (FIG. 1). The method 200 illustrates the steps of coupling two of the aseptic coupling devices 100 or two of the aseptic coupling devices 100' that are described above, for example.

In step 210, the covers of the two aseptic couplings to be mated to each other are removed from their home positions in which the covers are protecting the membranes of the aseptic couplings. For example, in some embodiments the covers are unlatched and then pivoted in relation to the main bodies of the aseptic couplings. When the covers are removed from their home positions, the membranes that maintain the sterility of the aseptic couplings are uncovered.

In step 220, the two aseptic couplings are engaged to each other to create a first pre-coupled configuration. In the first pre-coupled configuration, the membranes are lightly compressed between the seals of the aseptic couplings and the main bodies of the aseptic couplings are latched together.

In step 230, the membranes are removed from the aseptic couplings to create a second pre-coupled configuration. This can be performed, for example, by simultaneously pulling the membranes transversely away from the main bodies of the couplings (e.g., as depicted by arrow P in FIG. 31). When the membranes are removed, the front faces of the seals of the aseptic couplings then directly contact each other and lightly seal against each other. The sterility of the internal fluid flow paths of the aseptic couplings is/are thereby preserved.

In optional step 240, spacers are removed from the aseptic couplings. For example, in some embodiments the aseptic couplings include spacers such as the spacers 180 or 180' as described above.

In step 250, one or more latches (e.g., two latches) on the aseptic couplings are engaged to increase the compression between the seals of the aseptic couplings. In some embodiments, the latches lock in the latched position such that the latches cannot be unlatched (without destroying the latches or portions of the aseptic couplings). With the latches fully engaged, a sterile and fluid-tight connection between the aseptic couplings is created.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. An aseptic fluid coupling comprising:
a main body defining a longitudinal axis, a bore, and a fluid flow path through the main body along the longitudinal axis, the main body comprising:
a front face; and
a termination that is at an opposite end of the main body relative to the front face;
a seal member including a portion disposed within the bore and a portion extending from the front face around the longitudinal axis;
a latch movably coupled to the main body, the latch configured to clamp the main body of the aseptic fluid coupling to a second main body of a mated second aseptic fluid coupling such that: (i) the seal member is compressed to a degree that ensures leak-proof operation and (ii) a robust mechanical connection is created between the aseptic fluid coupling and the mated second aseptic fluid coupling;

a flexible membrane including a portion attached to the front face around the seal member to block contaminants from entering the fluid flow path, the membrane also including a tail end portion that is at an opposite end of the membrane in comparison to the portion attached to the front face; and a linkage rotatably coupled directly with the main body and rotatably coupled directly with the latch, wherein the linkage is configured to rotate about an axis perpendicular to the longitudinal axis of the main body to cause the latch to rotate relative to the main body.

2. The aseptic fluid coupling of claim 1, wherein the aseptic fluid coupling is configured for coupling with a second aseptic fluid coupling that is structurally identical to the aseptic fluid coupling.

3. The aseptic fluid coupling of claim 1, further comprising a cover attached to the tail end portion of the membrane and rotatably coupled with the main body.

4. The aseptic fluid coupling of claim 3, further comprising a cover guide slidably engaged with the cover and pivotably coupled with the main body, wherein the cover guide rotatably couples the cover with the main body.

5. The aseptic fluid coupling of claim 4, wherein the cover is slidably coupled with the cover guide.

6. The aseptic fluid coupling of claim 1, further comprising a spacer disposed between the main body and the latch so as to space the latch apart from the main body.

7. The aseptic fluid coupling of claim 1, wherein the main body includes two pre-coupling latch members on one side of the main body and two corresponding latch receptacles on an opposite side of the main body.

8. The aseptic fluid coupling of claim 1, wherein the main body includes a first final latch rib on one side of the main body and a second final latch rib on an opposite side of the main body.

9. The aseptic fluid coupling of claim 1, wherein the latch includes two first main body latch elements on one side of the latch and two second main body latch elements on an opposite side of the latch.

10. The aseptic fluid coupling of claim 9, wherein the latch includes a lock member between the first and second main body latch elements.

11. The aseptic fluid coupling of claim 1, further comprising a spacer disposed between the main body and the latch so as to space the latch apart from the main body, and wherein the spacer is releasably latched to a cover that is attached to the tail end portion of the membrane and rotatably coupled with the main body.

12. The aseptic fluid coupling of claim 1, wherein the main body includes two pre-coupling latch members on one side of the main body and a corresponding latch lock structure on an opposite side of the main body.

13. The aseptic fluid coupling of claim 1, wherein the linkage is not threaded.

14. The aseptic fluid coupling of claim 1, wherein the main body comprises at least one linkage attachment member, and wherein the linkage is rotatably coupled to the at least one linkage attachment member of the main body.

15. An aseptic fluid coupling comprising:
a main body defining a longitudinal axis, a bore, and a fluid flow path through the main body along the longitudinal axis, the main body comprising:
a front face; and
a termination that is at an opposite end of the main body relative to the front face;
a seal member including a portion disposed within the bore and a portion extending from the front face around the longitudinal axis;
a latch movably coupled to the main body, the latch configured to clamp the main body of the aseptic fluid coupling to a second main body of a mated second aseptic fluid coupling in a direction parallel with the longitudinal axis of the main body, such that: (i) the seal member is compressed to a degree that ensures leak-proof operation and (ii) a robust mechanical connection is created between the aseptic fluid coupling and the mated second aseptic fluid coupling; and
a flexible membrane including a portion attached to the front face around the seal member to block contaminants from entering the fluid flow path, the membrane also including a tail end portion that is at an opposite end of the membrane in comparison to the portion attached to the front face.

16. An aseptic fluid coupling comprising:
a main body defining a longitudinal axis, a bore, and a fluid flow path through the main body along the longitudinal axis, the main body comprising:
a front face; and
a termination that is at an opposite end of the main body relative to the front face;
a seal member including a portion disposed within the bore and a portion extending from the front face around the longitudinal axis;
a latch movably coupled to the main body, the latch configured to clamp the main body of the aseptic fluid coupling to a second main body of a mated second aseptic fluid coupling such that: (i) the seal member is compressed to a degree that ensures leak-proof operation and (ii) a robust mechanical connection is created between the aseptic fluid coupling and the mated second aseptic fluid coupling;
a flexible membrane including a portion attached to the front face around the seal member to block contaminants from entering the fluid flow path, the membrane also including a tail end portion that is at an opposite end of the membrane in comparison to the portion attached to the front face; and
a linkage rotatably coupled directly with the main body and rotatably coupled directly with the latch, wherein the linkage is configured to cause the latch to rotate relative to the main body as the latch is manipulated to clamp the main body of the aseptic fluid coupling to the second main body of the mated second aseptic fluid coupling.

* * * * *